United States Patent
Bernard-Pierrot et al.

(10) Patent No.: US 9,233,144 B2
(45) Date of Patent: Jan. 12, 2016

(54) TYROSINE KINASE RECEPTOR TYRO3 AS A THERAPEUTIC TARGET IN THE TREATMENT OF CANCER

(75) Inventors: Isabelle Bernard-Pierrot, Nogent sur Marne (FR); Francois Radvanyi, Fontenay aux Roses (FR); Yves Allory, Paris (FR); Nicolas Stransky, Le Kremlin Bicetre (FR)

(73) Assignees: INSTITUT CURIE, Paris (FR); CENTRE NATIONAL DE LA RECHERCHE SCIENTIFIQUE, Paris (FR); ASSISTANCE PUBLIQUE HOPITAUX DE PARIS, Paris (FR); UNIVERSITE PARIS-EST CRETEIL VAL DE MARNE, Creteil (FR)

( * ) Notice: Subject to any disclaimer, the term of this patent is extended or adjusted under 35 U.S.C. 154(b) by 0 days.

(21) Appl. No.: 13/062,804

(22) PCT Filed: Sep. 18, 2009

(86) PCT No.: PCT/EP2009/062091
§ 371 (c)(1), (2), (4) Date: Sep. 16, 2011

(87) PCT Pub. No.: WO2010/031828
PCT Pub. Date: Mar. 25, 2010

(65) Prior Publication Data
US 2012/0034167 A1    Feb. 9, 2012

(30) Foreign Application Priority Data
Sep. 19, 2008 (EP) ..................... 08305574

(51) Int. Cl.
| | | |
|---|---|---|
| A61K 6/00 | (2006.01) |
| A61K 31/00 | (2006.01) |
| A61K 31/70 | (2006.01) |
| A61K 31/7088 | (2006.01) |
| A61K 31/713 | (2006.01) |
| A61K 38/00 | (2006.01) |
| A61K 38/16 | (2006.01) |
| A61K 38/43 | (2006.01) |
| A61K 38/45 | (2006.01) |
| C07K 16/30 | (2006.01) |
| C12N 15/113 | (2010.01) |
| A61K 45/06 | (2006.01) |
| C12Q 1/48 | (2006.01) |
| G01N 33/50 | (2006.01) |
| G01N 33/574 | (2006.01) |

(52) U.S. Cl.
CPC .............. *A61K 38/45* (2013.01); *A61K 31/713* (2013.01); *A61K 38/005* (2013.01); *A61K 45/06* (2013.01); *C07K 16/3069* (2013.01); *C12N 15/1137* (2013.01); *C12Q 1/485* (2013.01); *C12Y 207/10001* (2013.01); *G01N 33/5011* (2013.01); *G01N 33/57407* (2013.01); *C12N 2310/11* (2013.01); *C12N 2310/14* (2013.01); *G01N 2500/00* (2013.01)

(58) Field of Classification Search
None
See application file for complete search history.

(56) References Cited

U.S. PATENT DOCUMENTS

| | | |
|---|---|---|
| 2007/0128200 A1 | 6/2007 | Yang et al. |
| 2009/0258855 A1 | 10/2009 | Bounaud et al. |

FOREIGN PATENT DOCUMENTS

| | | |
|---|---|---|
| WO | WO 2005/000207 A | 1/2005 |
| WO | WO 2007/013575 | 2/2007 |
| WO | WO 2007/044894 | 4/2007 |
| WO | WO 2008/051808 A | 5/2008 |
| WO | WO 2008/066498 A | 6/2008 |

OTHER PUBLICATIONS

Jacobsen KM, Linger RMA, Graham DK . TYRO3 (TYRO3 protein tyrosine kinase). Atlas Genet Cytogenet Oncol Haematol. Jan. 2010.*
Porta et al., "TK1258, a multi-targeted receptor tyrosine kinase (RTK) inhibitor, is efficacious in preclinical models of bladder cancer," proceedings of the American Association for Cancer Research Annual Meeting; vol. 49, Apr. 2008, p. 1164; & 99$^{th}$ Annual Meeting of the American-Association-For-Cancer-Research; San Diego, CA Apr. 12-16, 2008.
Kamat et al: Ci-1033, a pan-erbB tyrosine kinase antagonist, inhibits the growth of orthotopic bladder cancer tumors via direct effects on receptor phosphorylation and inhibition of angiogenesis, Journal of Urology, vol. 169, No. 4 Supplement, Apr. 2003, pp. 130-131 & 98$^{th}$ Annual Meeting of the American Urological Association, Chicago, IL, Apr. 26-May 2, 2003.
Schwartz G K et al,.: "A Protein Kinase C PKC Inhibitor Staurosporine Stsn Inhibits Invasion of Clinically Invasive Human Bladder Carcinoma Cells," Proceedings of the American Association for Cancer Research Annual Meeting, vol. 31, 1990, p. 74, & 81st Annual Meeting of the American Association for Cancer Research, Washington, D.C., USA, May 23-2.
Pearson et al: "A Phase II Study of Neoadjuvant Erlotinib (Tarceva) In Patients With Muscle-Invasive Bladder Cancer Undergoing Radical Cystectomy: Preliminary Results" Journal of Urology, Baltimore, MD, vol. 179, No. 4, Supplement, Mar. 19, 2008, p. 119.
Silay et al.,: "Sunitinib malate and sorafenib may be beneficial at the treatment of advanced bladder cancer due to their anti-angiogenic effects" Medical Hypotheses, Eden Press, Penrith, US, vol. 69, No. 4, Jan. 1, 2007, pp. 892-895.
Agarwal P K et al.,: "Emerging drugs for targeted therapy of bladder cancer," Expert Opinion on Emerging Drugs 200709 GB, vol. 12, No. 3, Sep. 2007, pp. 435-448.
International Search Report and Written Opinion of corresponding PCT Application No. PCT/EP2009/062091 dated Jan. 21, 2010.

* cited by examiner

Primary Examiner — Alana Harris Dent
(74) Attorney, Agent, or Firm — Saliwanchik, Lloyd & Eisenschenk

(57) ABSTRACT

The present invention concerns new methods for treating cancer by using TYRO3 inhibitors and methods for identifying new molecules of interest for treating cancer.

23 Claims, 14 Drawing Sheets

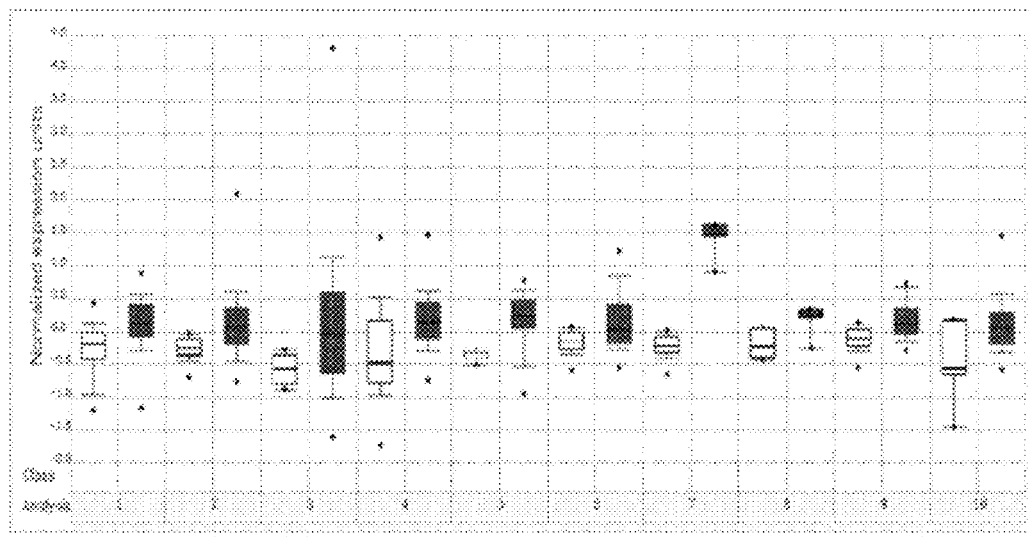

Figure 16A

| Analysis | study | Tissue | class 1 | class 2 | t-test p value |
|---|---|---|---|---|---|
| 1 | Sanchez-Carbayo et al., J Clin Oncol (2006) 5 : 778-789 | Bladder | Normal Bladder (48) | Bladder Carcinoma (109) | 3.70E-09 |
| 2 | Basso et al., Nat Genet. (2005) 4 : 382-392 | Lymphoma | Normal B-Cells (25) | Diffuse Large B-Cell Lymphoma (89) | 1.80E-07 |
| 3 | Rosenwald et al., N Engl J Med. (2002)25 : 1937-1947 | Lymphoma | Normal Blood CD19+ B-Cells (6), Normal Germinal Center B-Cells (4) | Diffuse Large B-Cell Lymphoma (274) | 3.30E-06 |
| 4 | Alizadeh et al., Nature (2000 ) 6769 : 503-511 | Lymphoma | Benign Lymphoid (31) | Diffuse Large B-Cell Lymphoma (66) | 3.60E-04 |
| 5 | Frierson et al., Am J Pathol. (2002) 4 : 1315-1323 | Salivary Gland | Normal Salivary Gland (6) | Adenoid Cystic Carcinoma Of Salivary Gland (15) | 4.90E-04 |
| 6 | Basso et al., Nat Genet. (2005) 4 : 382-392 | Lymphoma | Normal B-Cells (25) | Burkitt Lymphoma (31) | 0.001 |
| 7 | Basso et al., Nat Genet. (2005) 4 : 382-392 | Lymphoma | Normal B-Cells (25) | Multiple Myeloma (4) | 0.002 |
| 8 | Buchholz et al., Oncogene (2005) 44 : 6626-6636 | Pancreas | Normal Pancreas Ducts (6) | Pancreatic Ductal Adenocarcinoma (8) | 0.003 |
| 9 | Basso et al., Nat Genet. (2005) 4 : 382-392 | Lymphoma | Normal B-Cells (25) | Hairy Cell Leukemia (16) | 0.003 |
| 10 | Rosenwald et al., N Engl J Med. (2002)25 : 1937-1947 | Lymphoma | Normal B-Cells (6) | Diffuse Large B-Cell Lymphoma (36) | 0.009 |

Figure 16B

SEQUENCE LISTING

```
<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: siRNA anti-TYRO3

<400> SEQUENCE: 1
ggugugccau uuuucacagt t                                             21

<210> SEQ ID NO 2
<211> LENGTH: 21
<212> TYPE: DNA
<213> ORGANISM: Artificial Sequence
<220> FEATURE:
<223> OTHER INFORMATION: Control siRNA

<400> SEQUENCE: 2
ggcaagauuc uucucguugt t                                             21
```

TYROSINE KINASE RECEPTOR TYRO3 AS A THERAPEUTIC TARGET IN THE TREATMENT OF CANCER

RELATED APPLICATIONS

This application is the U.S. National Phase filing under 35 U.S.C. §371 of PCT/EP2009/062091, filed Sep. 18, 2009, entitled "TYROSINE KINASE RECEPTOR TYRO3 AS A THERAPEUTIC TARGET IN THE TREATMENT OF CANCER", which designated the United States and was published in English on Mar. 25, 2010, which claims priority under 35 U.S.C. §119(a)-(d) to European Patent Application No. 08305574.9, filed Sep. 19, 2008.

FIELD OF THE INVENTION

The present invention relates to the field of medicine, in particular to the treatment of cancer. It relates to new methods of treatment of cancer and to methods of screening of molecules useful in the treatment of cancer.

BACKGROUND OF THE INVENTION

Cancer occurs when cell division gets out of control and results from impairment of a DNA repair pathway, the transformation of normal genes into oncogenes or the malfunction of tumor supressor genes. Many different forms of cancer exist. The incidence of these cancers varies but it represents the second highest cause of mortality, after heart disease, in most developed countries.

Bladder cancer is the fifth cancer in term of incidence. It can appear as superficial lesions restricted to the urothelium (Ta and carcinoma in situ (CIS)) or to the lamina propria (T1) or as muscle invasive lesions (T2-T4). Two different pathways of tumour progression have been so far described in bladder cancer, the Ta pathway and the CIS pathway. Ta tumours which constitute 50% of bladder tumours at first presentation are superficial papillary tumour usually of low grade which do not invade the basal membrane. Carcinoma-in-situ (CIS) are also superficial tumour which do not invade the basal membrane but are always of high grade. Ta tumours, despite chirurgical resection associated or not with BCG (Bacillus Calmette-Guerin) therapy, often recur but rarely progress to muscle invasive disease (T2-T4), whereas CIS often progress to T2-T4 tumors. Concerning muscle invasive bladder carcinomas, the standard treatment is cystectomy. Despite this radical treatment, muscle invasive bladder carcinoma remains a deadly disease for most patients.

Up to now, even if many recurrent chromosomal alterations have been described in bladder cancer, only few genes have been demonstrated to be implicated in tumor progression (p53, CDKN2A, RB1, E2F3, FGFR3).

Accordingly, there is a significant need for an appropriate bladder tumor treatment, in particular for new and more effective therapeutic agents.

SUMMARY OF THE INVENTION

The inventors surprisingly demonstrate herein that TYRO3 is over-expressed in several types of tumors including bladder tumors and is responsible for tumor cell survival. Furthermore, they show that compounds inducing inhibition or depletion of TYRO3 can be used to treat TYRO3 over-expressing cancers.

The present invention provides new therapeutic agents for treating cancer, and in particular bladder tumor.

In a first aspect, the present invention concerns an inhibitor of TYRO3 tyrosine kinase for use in the treatment of a TYRO3 over-expressing cancer. In a particular embodiment, the TYRO3 over-expressing cancer is selected from the group consisting of bladder tumor, diffuse large B-Cell lymphoma, adenoid cystic carcinoma of salivary gland, Burkitt lymphoma, multiple myeloma, pancreatic ductal adenocarcinoma, hairy cell leukemia, metastatic prostate cancer, melanoma and colorectal cancer. In a preferred embodiment, the TYRO3 over-expressing cancer is a bladder tumor.

The present invention also concerns a pharmaceutical composition comprising an inhibitor of TYRO3 tyrosine kinase and a pharmaceutically acceptable carrier/excipient for use in the treatment of a TYRO3 over-expressing cancer. In a particular embodiment, the TYRO3 over-expressing cancer is selected from the group consisting of bladder tumor, diffuse large B-Cell lymphoma, adenoid cystic carcinoma of salivary gland, Burkitt lymphoma, multiple myeloma, pancreatic ductal adenocarcinoma, hairy cell leukemia, metastactic prostate cancer, melanoma and colorectal cancer. In a preferred embodiment, the TYRO3 over-expressing cancer is a bladder tumor.

The TYRO3 tyrosine kinase inhibitor is preferably selected from the group consisting of, an antibody directed against the extracellular domain of TYRO3, a nucleic acid molecule interfering specifically with TYRO3 expression, a TYRO3 soluble bait, a dominant negative receptor presenting a kinase dead domain and a small molecule inhibiting the TYRO3 tyrosine kinase activity. In a preferred embodiment, the TYRO3 tyrosine kinase inhibitor is selected from the group consisting of an antibody directed against the extracellular domain of TYRO3, a nucleic acid molecule interfering specifically with TYRO3 expression, a TYRO3 soluble bait and a dominant negative receptor presenting a kinase dead domain. In a particular embodiment, the TYRO3 tyrosine kinase inhibitor is a RNAi, an antisense nucleic acid or a ribozyme interfering specifically with TYRO3 expression.

In a preferred embodiment, the inhibitor is a siRNA, in particular siRNA comprising a sequence of SEQ ID No. 1.

In another embodiment, the inhibitor is a TYRO3 soluble bait. In a particular embodiment, the TYRO3 soluble bait is a recombinant TYRO3 receptor constituted of, at least, the extracellular domain of the receptor or one of the domain (Ig like or fibronectin) thereof. In another particular embodiment, the TYRO3 soluble bait is an antibody directed against Gas-6.

In one embodiment, the TYRO3 tyrosine kinase inhibitor is used in combination with another active ingredient, in particular an antitumoral drug. In a particular embodiment, the TYRO3 tyrosine kinase inhibitor is used in combination with a bladder tumor treatment.

In another aspect, the present invention concerns a method for screening or identifying a molecule suitable for treating a TYRO3 over-expressing cancer, wherein the method comprises the steps of (i) contacting candidate molecules with TYRO3 receptor, and (ii) selecting molecules having the ability to bind to TYRO3 receptor and/or to compete with and/or for a ligand of TYRO3 receptor and/or to decrease the phosphorylation of the TYRO3 substrates or the TYRO3 autophosphorylation. In a particular embodiment, the TYRO3 over-expressing cancer is a bladder tumor.

The present invention also concerns a method for screening or identifying a molecule suitable for treating a TYRO3 over-expressing cancer, wherein the method comprises the steps of (i) contacting candidate molecules with cells expressing TYRO3 receptor, and (ii) selecting molecules having the ability to bind to TYRO3 receptor and/or to compete with and/or for a ligand of TYRO3 receptor and/or to decrease the TYRO3 gene expression and/or to decrease the phosphorylation of the TYRO3 substrates or the TYRO3 autophosphorylation. In a particular embodiment, the TYRO3 over-expressing cancer is a bladder tumor.

These methods for screening or identifying a molecule suitable for treating a TYRO3 over-expressing cancer can optionally further comprise the step of administering in vitro selected molecule in a TYRO3 over-expressing tumor non human animal model and analyzing the effect on the disease progression. In a particular embodiment, the TYRO3 over-expressing cancer is a bladder tumor and the TYRO3 over-expressing tumor non human animal model is a bladder tumor non human animal model.

The present invention further concerns a method for treating a TYRO3 over-expressing cancer in a subject, wherein the method comprises the step of administering a therapeutically efficient amount of a TYRO3 tyrosine kinase inhibitor to the subject.

In a particular embodiment, the TYRO3 over-expressing cancer is selected from the group consisting of bladder tumor, diffuse large B-Cell lymphoma, adenoid cystic carcinoma of salivary gland, Burkitt lymphoma, multiple myeloma, pancreatic ductal adenocarcinoma, hairy cell leukemia, metastactic prostate cancer, melanoma and colorectal cancer. In a preferred embodiment, the TYRO3 over-expressing cancer is a bladder tumor.

Finally, the present invention concerns the use of a TYRO3 tyrosine kinase inhibitor for the preparation of a medicament for the treatment of a TYRO3 over-expressing cancer. In a particular embodiment, the TYRO3 over-expressing cancer is selected from the group consisting of bladder tumor, diffuse large B-Cell lymphoma, adenoid cystic carcinoma of salivary gland, Burkitt lymphoma, multiple myeloma, pancreatic ductal adenocarcinoma, hairy cell leukemia, metastactic prostate cancer, melanoma and colorectal cancer. In a preferred embodiment, the TYRO3 over-expressing cancer is a bladder tumor.

Cells were incubated 72 h in presence of various concentrations of a polyclonal antibody directed against the extra-cellular domain of TYRO3 (goat Anti-Rse (N-18), Santa-Cruz biotechnology) and cell viability was measured by MTT assay.

Figure 7:
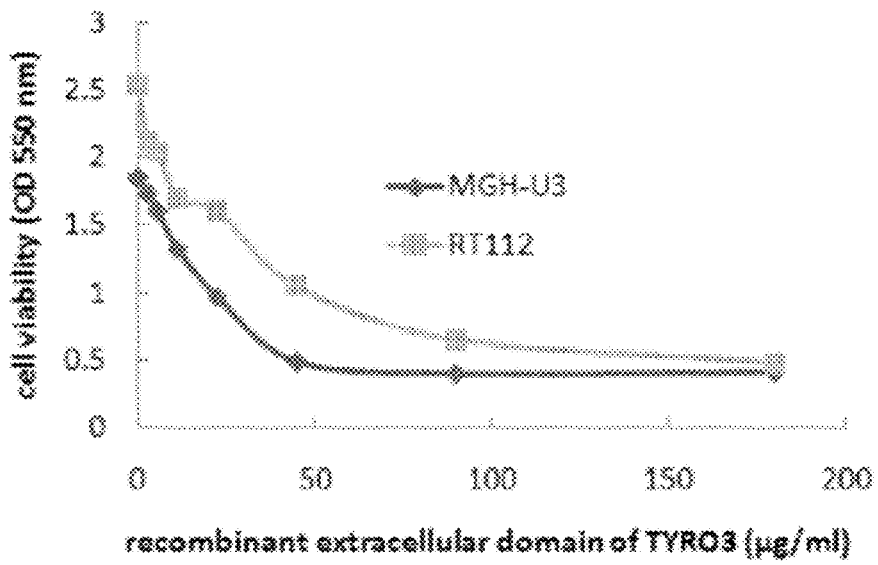

FIG. 7 shows the effect of a recombinant soluble TYRO3 receptor on cell viability. The extra-cellular domain of TYRO3 (421 aa) composed of two Ig like domains (aa 1-220) and two fibronectin III domain (aa 220-421) was produced in bacteria and purified. Cells were incubated 72 h in presence of various amounts of this soluble receptor and cell viability was measured by MTT incorporation.

Figure 8:
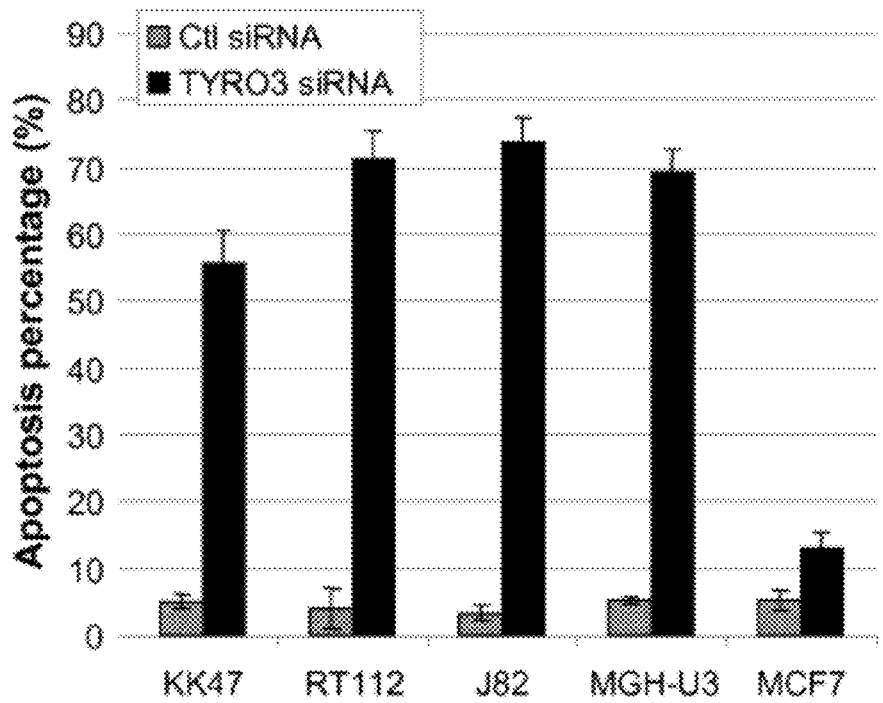

FIG. 8 shows the results of a TUNEL assay on transfected bladder cancer cells. $3 \times 10^4$ cells per well were seeded on a glass slide in a 24-well plate and transfected with 50 nM siRNA. DNA fragmentation was evaluated 72 hours after transfection, using a TUNEL (deoxynucleotidyl transferase (Tdt)-mediated nick-end labeling) assay detection Kit (Roche Diagnostic, Meylan, France) according to the manufacturer's instructions. The inventors analyzed 600 cells under a light microscope, determining the proportion of labeled cells.

Figure 9:
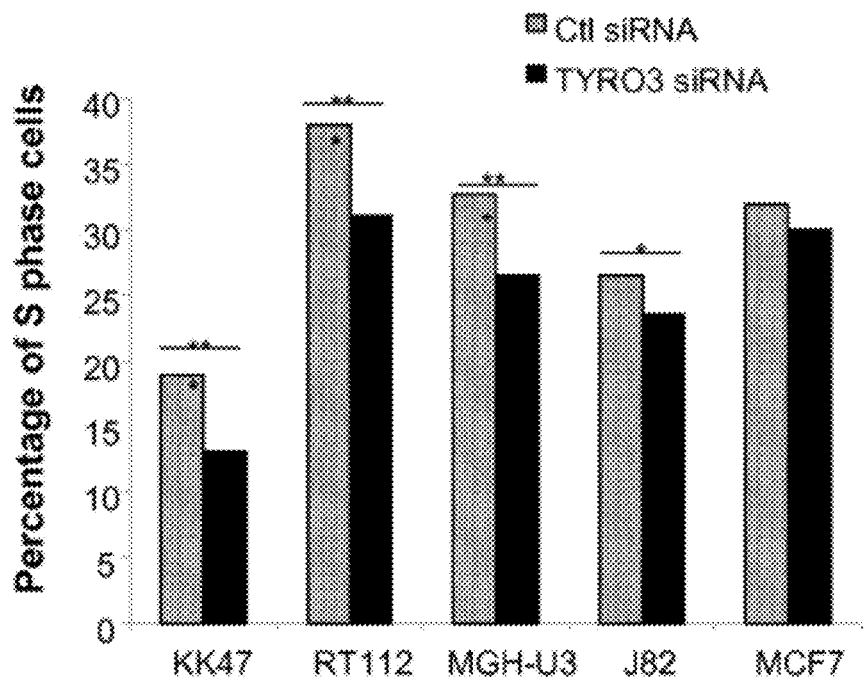
Figure 10:
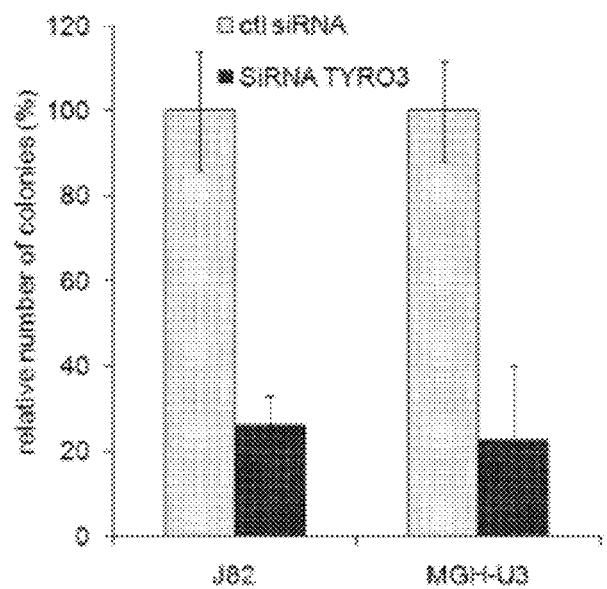

FIG. 9 shows cell cycle analysis by flow-cytometry 72 h post siRNA transfection. Results were analyzed using Fisher test, *** $p<0.001$, * $0.01<p<0.05$ FIG. 10 shows a graph representing the effect of TYRO3 knockdown on anchorage-independent colony formation. $2.10^4$ 50 nM siRNA-transfected cells in DMEM supplemented with 10% FCS and 0.3% agar, were added to triplicate wells containing medium and 0.8% agar on 12-well plates. The plates were incubated for two weeks and colonies with diameters greater than 50 µm were scored as positive, using a phase-contrast microscope equipped with a measuring grid. Results are the means+/−SD of two independent experiments carried out in triplicate.

Figure 11A:
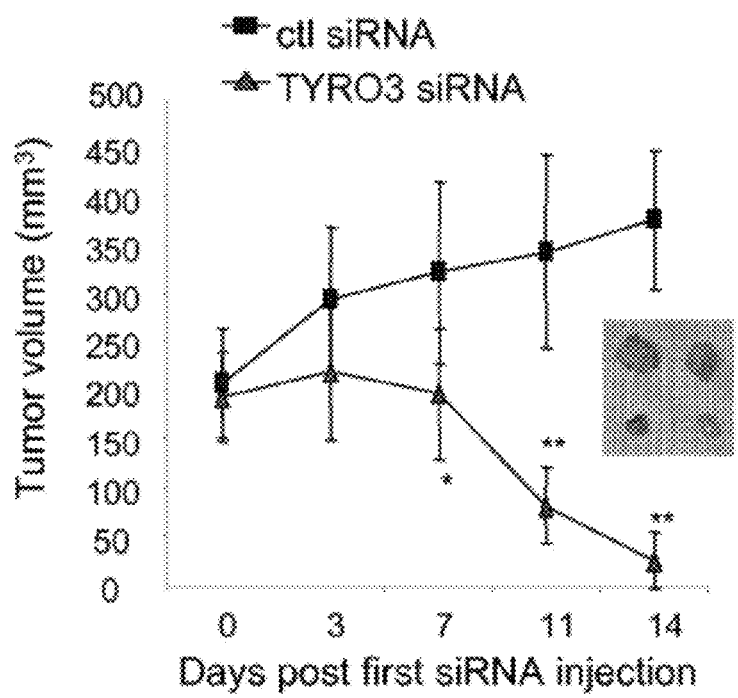
Figure 11B:
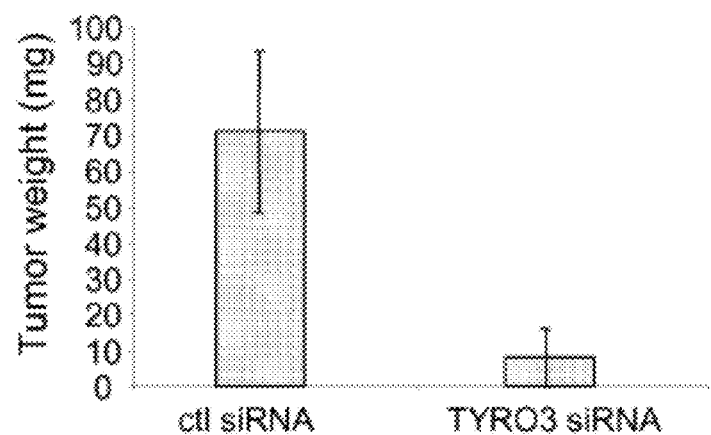

FIG. 11 shows the effect of TYRO3 siRNA on the growth of xenografted J82 tumors. Tumor-bearing mice were treated three times a week by intraperitoneal injection of 4 µg siRNA (control or TYRO3) (6 mice and 12 tumors per group) (The first injection corresponds to day 0). Tumor volume variations are represented on the graph of FIG. 11A. (Wilcoxon rank sum test: *, $0.05<p<0.01$; , $0.01<p<0.001$; *, $p<0.001$) Inset are pictures of representative tumors observed at the end of the treatment. The upper line tumors are those of control siRNA treated mice. The lower line tumors are those of TYRO3 siRNA treated mice. Tumors were weighted at the end of the experiment (FIG. 11B).

Figure 12A:
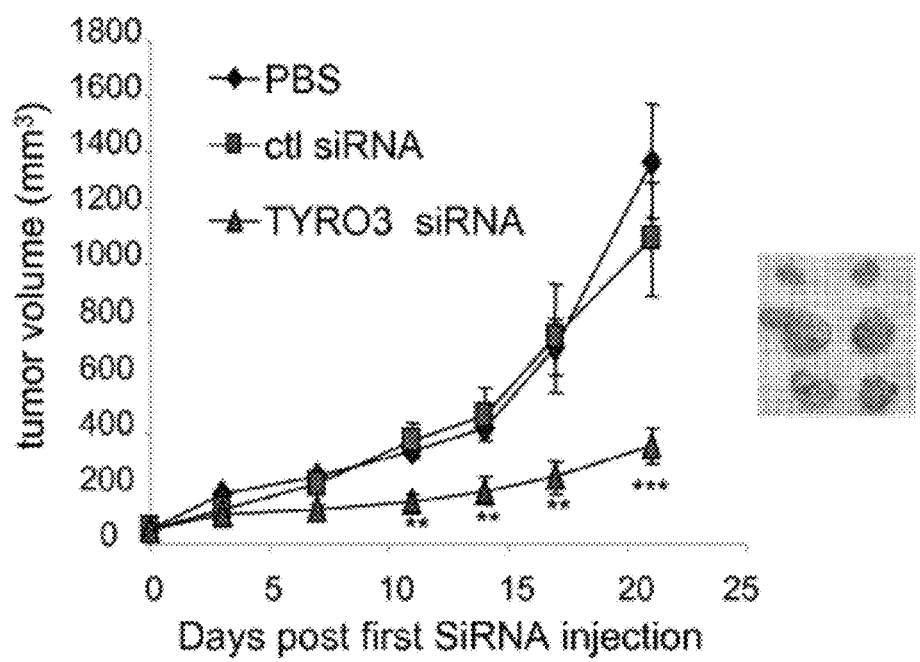
Figure 12B:
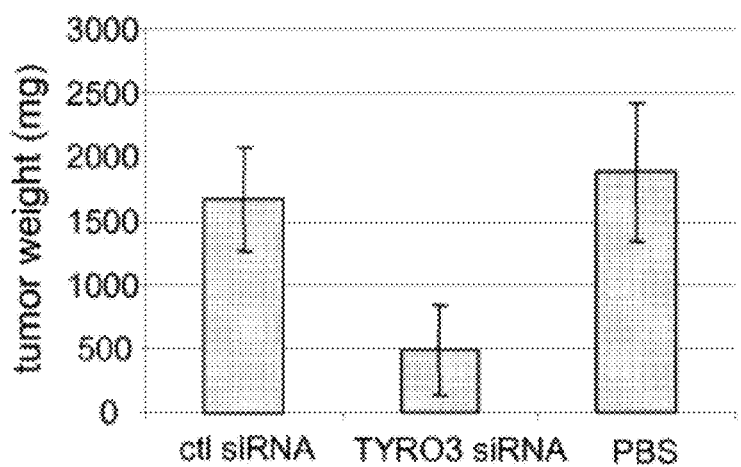

FIG. 12 shows the effect of TYRO3 siRNA on the growth of xenografted J82 tumors. Tumor-bearing mice were treated three times a week by intraperitoneal injection of 4 µg siRNA (control or TYRO3) (6 mice and 12 tumors per group) (The first injection corresponds to day 0). Tumor volume variations are represented on the graph of FIG. 12A. (Wilcoxon rank sum test: *, $0.05<p<0.01$, , $0.01<p<0.001$, *, $p<0.001$) Inset are pictures of representative tumors observed at the end of the treatment. The upper line tumors are those of TYRO3 siRNA treated mice. The middle line tumors are those of control siRNA treated mice. The lower line tumors are those of PBS treated mice. Tumors were weighted at the end of the experiment (FIG. 12B).

Figure 13:
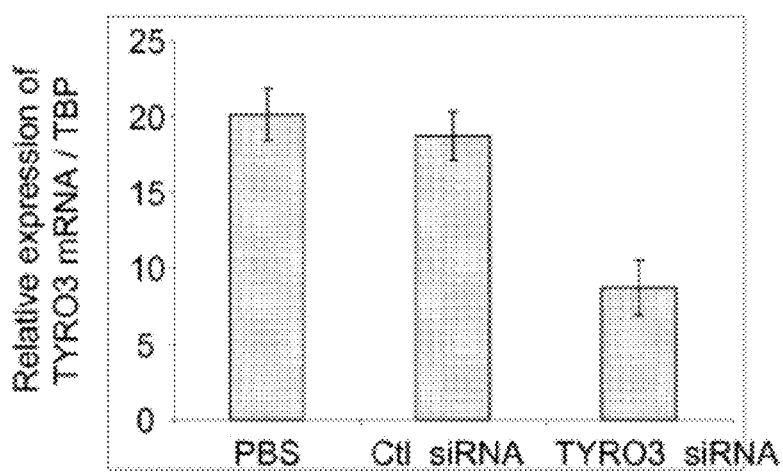

FIG. 13 is a graph showing TYRO3 mRNA levels for MGH-U3 xenografts, 3 days after the last siRNA injection, divided by TBP (TATA binding protein) mRNA levels+/−SD in treated and control tumors, as assessed by Q-RT-PCR.

Figure 14A:
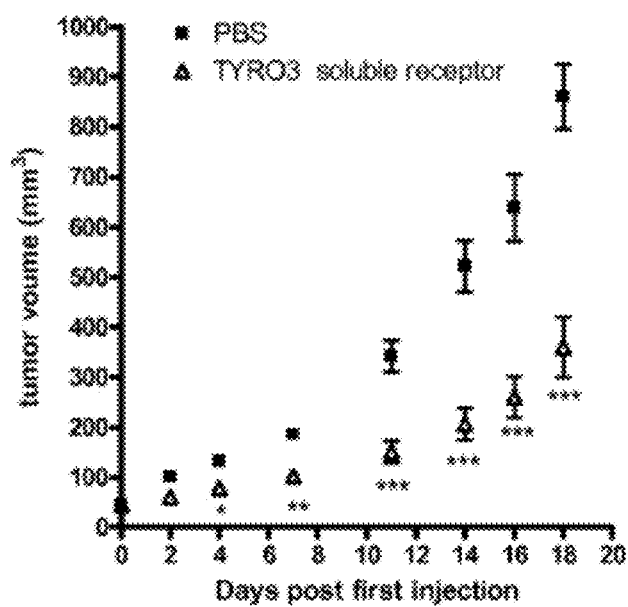
Figure 14B:
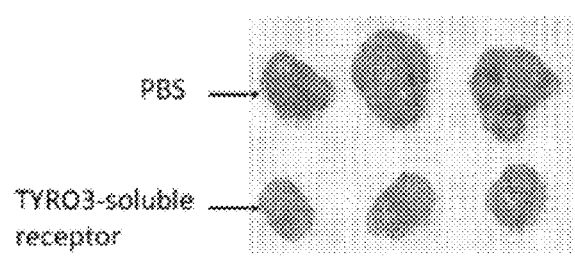

FIG. 14 shows the effect on the growth of xenografted MGH-U3 tumors of TYRO3 recombinant soluble receptor consisting of the recombinant extracellular domain of TYRO3 produced in bacteria. Tumor-bearing mice were treated three times a week by intratumoral injection of 80 µg TYRO3-soluble receptor or PBS (7 mice and 14 tumors per group) (The first injection corresponds to day 0). Tumor volume variations are represented on the graph of FIG. 14A. (Wilcoxon rank sum test: *, $0.05 < p < 0.01$; , $0.01 < p < 0.001$; *, $p < 0.001$). Pictures of representative tumors observed at the end of the treatment are shown in FIG. 14B.

Figure 15:
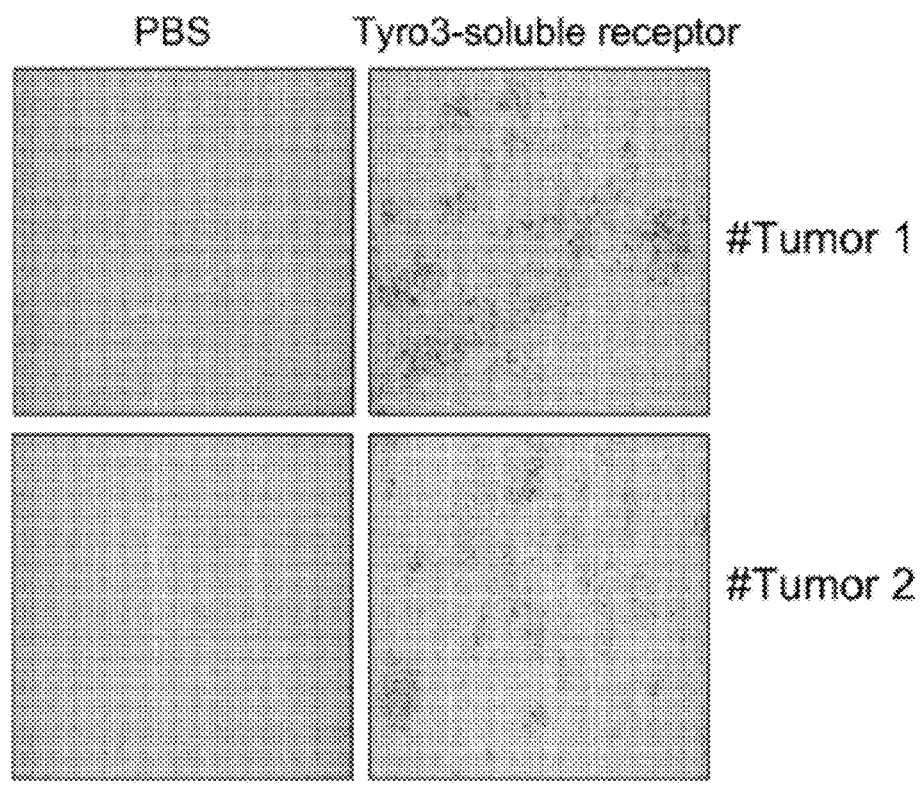

FIG. 15 shows the results of a TUNEL assay on xenografted MGH-U3 tumors treated with TYRO3-soluble receptor or PBS. 18 days after the beginning of the treatment mice were sacrificed and Tumors were paraffin embedded. DNA fragmentation was then evaluated using a TUNEL (deoxynucleotidyl transferase (Tdt)-mediated nick-end labeling) assay detection Kit (Roche Diagnostic, Meylan, France) according to the manufacturer's instructions. Pictures of representative fields observed are shown.

FIG. 16 shows TYRO3 over-expression in different cancers. Differential expression analyses of TYRO3 in human tumors using Oncomine's web site (Rhodes et al., 2004). Studies showing significant upregulation ($p < 0.01$) of TYRO3 gene expression levels in tumor (grey, right panel) as compared to normal (white, left panel) tissues are represented (FIG. 16A). Details on the data used for this analysis are provided in FIG. 16B.

Figure 17:
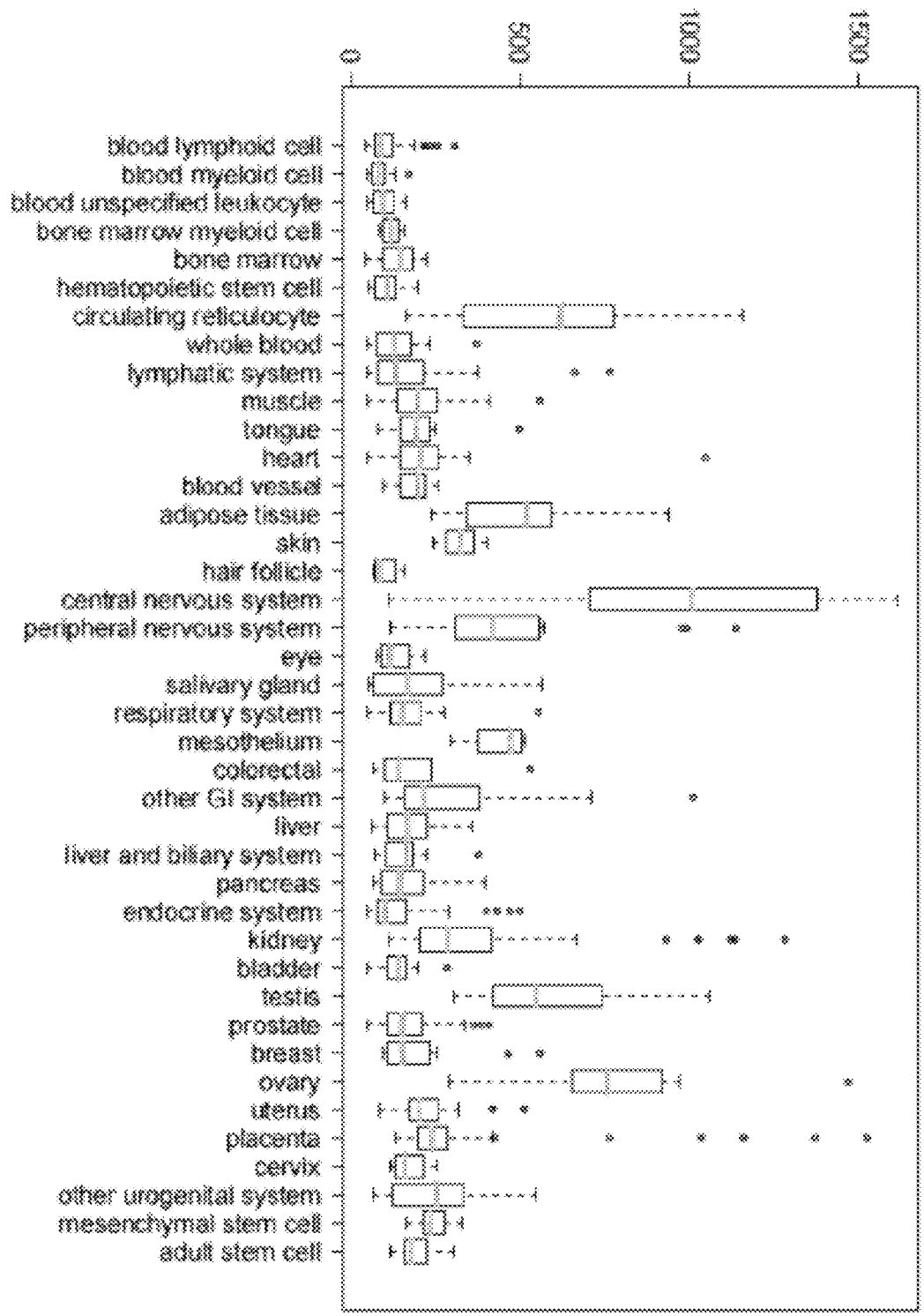

FIG. 17 shows plots of TYRO3 gene expression across a large spectrum of normal tissues (FIG. 16B) extracted from GeneSapiens DataBase (Kilpinen et al., 2008).

Figure 18:

FIG. 18 shows plots of TYRO3 gene expression across a large spectrum of tumoral tissues extracted from GeneSapiens DataBase (Kilpinen et al., 2008).

DETAILED DESCRIPTION OF THE INVENTION

By analysing the transcriptome in a series of 80 bladder carcinomas, 5 normal bladder urothelium and 10 bladder tumour cell lines, the inventors have:
 identified a tyrosine kinase receptor TYRO3 overexpressed in almost 70% of bladder carcinoma as compared to normal urothelium samples, this over-expression being independent of stage and grade;
 noticed that one of the TYRO3 ligands, GAS6, is also over-expressed in invasive carcinoma as compared to normal urothelium and superficial tumors; and,
 functionally demonstrated the importance of TYRO3 in bladder tumors cell survival.

QPCR analysis validated Affymetrix transcriptomic data and showed hence an over-expression of TYRO3 in most bladder tumor samples. In situ hybridization demonstrated that TYRO3 is expressed by bladder tumor epithelial cells whereas GAS6 is mainly expressed by stromal cells. Functional studies of TYRO3 in four bladder tumor cell lines (two expressing only TYRO3 and two expressing both TYRO3 and GAS6) using siRNA to knock down gene expression or a recombinant TYRO3 soluble receptor (constituted of the extracellular domain of the receptor) showed that TYRO3 was necessary for in vitro bladder cancer cell survival. These results were confirmed in vivo by using a xenografted human bladder tumor derived cell line. Indeed, inactivation of TYRO3 1) inhibits cell survival by inducing cell apoptosis; 2) inhibits anchorage independent growth demonstrating that TYRO3 regulates cell survival of clonogenic cells; 3) inhibits growth of bladder tumour cells xenografted in nude mice and even more reduces the size of tumor. Interestingly, the inventors observed the same in vitro effect through TYRO3 activity inhibition using a polyclonal anti-TYRO3 antibody directed against its extracellular domain.

Furthermore, the inventors demonstrated that TYRO3 is not only over-expressed in bladder tumors but also in several other types of cancer such as diffuse large B-Cell lymphoma, adenoid cystic carcinoma of salivary gland, Burkitt lymphoma, multiple myeloma, pancreatic ductal adenocarcinoma, hairy cell leukemia, metastactic prostate cancer, melanoma and colorectal cancer.

Accordingly, TYRO3 has been demonstrated by the inventors to be a tyrosine kinase overexpressed in most bladder tumors and several other types of cancers and to induce tumor cell survival. Therefore, the present invention provides a new interesting therapeutic target in TYRO3 over-expressing cancer, and in particular in bladder cancer.

Up to now, TYRO3 has been described to be over-expressed or co-expressed with its ligand in few human tumor types (uterine liomyoma (Sun et al., 2003a), uterine endometrial cancers and ovarian endometriose (Sun et al., 2002, Sun et al., 2003b), lung carcinoma (Wimmel at al., 1999)) but its role in tumor progression and especially in tumor cell survival has never been suggested nor demonstrated.

Its oncogenic role has been suggested since its expression transformed Rat-2 fibroblasts and RatB1 fibroblast (lai et al., 2004; Taylor et al., 1995). Furthermore, these oncogenic properties have also been suggested as a hybrid receptor constituted of the extracellular of the EGF receptor and the intracellular part of TYRO3 can transform NIH3T3 cells in presence of EGF (lan et al., 2000).

However, the potential oncogenic role of TYRO3 does not disclose nor suggest the role of this receptor in the tumor cell survival.

Recently, a withdrawn patent application (WO2005000207) by Kiener et al. suggests that TYRO3 is the receptor of PCDGF (PC cell derived growth factor). Since PCDGF is overexpressed in different cancers, this document suggests that inhibiting PCDGF binding to TYRO3 could be a therapeutic approach in several cancers overexpressing PCDGF. However, this document does not contain any data supporting their approach. Indeed, there is no data demonstrating that TYRO3 is the receptor of PCDGF and that a molecule inhibiting the potential binding of PCDGF to TYRO3 may have an effect of cancer cells.

Accordingly, for the first time, the role of TYRO3 in the tumor cell survival has been described and proved and this role provides a new means to treat an existing TYRO3 over-expressing cancer, and in particular bladder tumor.

Tyrosine kinase receptors are composed of an extracellular domain, which is able to bind a specific ligand, a transmembrane domain, and an intracellular catalytic domain, which is able to bind and phosphorylate selected intracellular substrates. Binding of a ligand to the extracellular region causes a series of structural rearrangements in the tyrosine kinase receptor that lead to its enzymatic activation triggering a cascade of events through phosphorylation of intracellular proteins that ultimately transduces the extracellular signal to the nucleus, causing changes in gene expression.

TYRO3 tyrosine kinase is a member of the AXL/Ufo/Mer tyrosine kinase receptor family. TYRO3 is also known as BYK, Brt, Dtk, Rse, Sky or Tif. Gas6 (growth arrest specific gene-6) and protein S have been described to activate TYRO3 tyrosine kinase activity.

The polynucleotide and amino acid sequences are well-known in the art. Reference sequences are Genbank Accession Nos MN_006293.2 and NP_006284.2, respectively.

The reference entry for human TYRO3 in the transcriptome database UniGene is Hs.381282.

In the present invention, an "inhibitor of TYRO3 tyrosine kinase" is a molecule which inhibits or reduces the activity of the TYRO3 receptor. Thus, the inhibitor induces the suppression or the reduction of the transmission of extracellular signals into the cell through the TYRO3 receptor.

The activity of TYRO3 tyrosine kinase activity can be easily assayed by any method known in the art. A first assay can be the determination of the ability of the inhibitor to bind the TYRO3 receptor. A second assay can be the determination of the ability of the inhibitor to compete with a ligand of the TYRO3 receptor for the binding of this receptor or of this ligand. A third assay can be the determination of the ability of the inhibitor to decrease the TYRO3 expression level. A fourth assay can be the determination of the ability of the inhibitor to decrease the phosphorylation of the TYRO3 substrates or the TYRO3 autophosphorylation. These different methods are described below in this document and can be combined.

The inhibition can be due to the binding of a molecule on the extracellular domain of the receptor. In this case, the inhibitor can be an antagonist which binds to the ligand binding domain or another domain of the receptor, or a molecule which modifies the activity of the receptor by steric hindrance or modification. This inhibitor can be, for instance, a small molecule, an aptamer or an antibody directed against the extracellular domain of the receptor. The inhibitory activity can be determined through a binding assay, a competitive binding assay or a phosphorylation assay.

The inhibition can also be due to the reduction or suppression of the expression of the gene coding for the receptor, for example by using specific RNAi, antisense or ribozyme, which induces a decrease of the number of receptors at the cell surface and thus a reduction of the extracellular signal transmission. The inhibitory activity can be assayed through the measure of the expression level of TYRO3, at the protein level or RNA level. The inhibitory activity can also be assayed through the phosphorylation of TYRO3 or TYRO3 substrate.

The use of baits which bind ligands of the TYRO3 receptor can also induce reduction or suppression of the activity of this receptor by competition for these ligands. Indeed, these baits trap ligands of TYRO3 and, consequently, decrease the concentration of available ligands for TYRO3 activation. These baits can be disposed in the membrane such as dominant negative receptors or in the extracellular fluid such as soluble receptor. These baits can also be antibodies directed against TYRO3 ligands. The inhibitory activity can be determined through a competition assay in order to determine the decrease of binding between the functional TYRO3 receptor and its ligand. The inhibitory activity can also be assayed through the phosphorylation of TYRO3 or TYRO3 substrate.

In particular embodiments of the present invention, the inhibitor of TYRO3 tyrosine kinase is preferably selected from the group consisting of a small molecule inhibiting the tyrosine kinase activity, an antibody directed against the extracellular domain of TYRO3, a nucleic acid molecule interfering specifically with TYRO3 expression, a dominant negative receptor presenting a kinase dead domain and a TYRO3 soluble bait.

In a preferred embodiment, the inhibitor of TYRO3 tyrosine kinase is preferably selected from the group consisting of a nucleic acid molecule interfering specifically with TYRO3 expression, an antibody directed against the extracellular domain of TYRO3, a dominant negative receptor presenting a kinase dead domain and a TYRO3 soluble bait.

As used herein, the term "small molecule inhibiting the tyrosine kinase activity" refers to small molecule that can be an organic or inorganic compound, usually less than 1000 daltons, with the ability to inhibit or reduce the activity of the TYRO3 tyrosine kinase. This small molecule can be derived from any known organism (including, but not limited to, animals, plants, bacteria, fungi and viruses) or from a library of synthetic molecules. Small molecules inhibiting the TYRO3 tyrosine kinase activity can be identify with the method further describe in this document.

In a particular embodiment, this molecule is selected from the group consisting of CHIR-258/TKI-258 (Novartis Pharmaceuticals), CI-1033 (Pfizer Pharmaceuticals), EKB-569 (Wyeth Pharmaceuticals), Erlotinib/Tarceva® (OSI Pharmaceuticals), MLN-8054(Millennium Pharmaceuticals), staurosporine (Calbiochem), SU-14813 (Pfizer Pharmaceuticals), Sunitinib/sutent® (Pfizer Pharmaceuticals) and ZD-6474 (AstraZeneca Pharmaceuticals) (see also Karaman et al., 2008).

As used herein, the term "antibody" is intended to refer broadly to any immunologic binding agent such as IgG, IgM, IgA, IgD and IgE, and humanized or chimeric antibody. In certain embodiments, IgG and/or IgM are preferred because they are the most common antibodies in the physiological situation and they are most easily manufactured. The term "antibody" is used to refer to any antibody-like molecule that has an antigen binding region, and includes antibody fragments such as Fab', Fab, F(ab') 2, single domain antibodies (DABs), Fv, scFv (single chain Fv), and the like. The techniques for preparing and using various antibody-based constructs and fragments are well known in the art. Means for preparing and characterizing antibodies are also well known in the art (See, e.g., Harlow and Lane, 1988).

A "humanized" antibody is an antibody in which the constant and variable framework region of one or more human immunoglobulins is fused with the binding region, e.g. the CDR, of an animal immunoglobulin. "Humanized" antibodies contemplated in the present invention are chimeric antibodies from mouse, rat, or other species, bearing human constant and/or variable region domains, bispecific antibodies, recombinant and engineered antibodies and fragments thereof. Such humanized antibodies are designed to maintain the binding specificity of the non-human antibody from which the binding regions are derived, but to avoid an immune reaction against the non-human antibody.

A "chimeric" antibody is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

Particularly, the term "antibody against the extracellular domain of TYRO3" designates an antibody as described above which is able to bind to the extracellular domain of the TYRO3 tyrosine kinase receptor and to block or reduce its activity. This inhibition can be due to steric hindrance or modification which prevents ligand binding.

In a preferred embodiment, the antibody directed against the extracellular domain of TYRO3 is an Anti-Rse (N-18) antibody (Santa-Cruz biotechnology).

As used herein, a "dominant negative receptor presenting a kinase dead domain" is a receptor which is able to bind to a ligand but is defective for the transmission of the signal.

Consequently, the over-expression of a dominant-negative receptor affects receptor signalling by blocking signal transduction. The presence of such dominant negative receptor at the cell surface induces a competition for ligand decreasing the amount of available ligand for the active receptor and thus preventing the activation of this receptor. In the present invention, the dominant negative receptor TYRO3 presents an operational extracellular domain which binds a ligand of TYRO3 and a non-operational kinase domain which is unable to transmit the signal inside the cell via phosphorylation of intracellular substrates.

As used herein, the term "TYRO3 soluble bait" designates an extracellular molecule which is able to bind to a TYRO3 ligand and thus to induce reduction or suppression of the activity of TYRO3 receptor by competition for its ligands or by heterodimerization with the wild type endogenous receptor. This soluble bait can be constituted of any peptide which has the ability to bind a ligand of the TYRO3 receptor or the extra-cellular domain of the receptor.

In one embodiment, the TYRO3 soluble bait is a recombinant TYRO3 receptor constituted of the extracellular domain of the receptor, or a fragment thereof able to bind to a TYRO3 ligand or an TYRO3 extracellular domain (e.g., Ig like or fibronectin domain). In a preferred embodiment, the TYRO3 soluble bait is the entire extracellular domain of TYRO3 receptor. The extra-cellular domain of TYRO3 (421 aa) is composed of two Ig like domains (aa 1-220) and two fibronectin III domains (aa 220-421). In another embodiment, the TYRO3 soluble bait is a recombinant TYRO3 receptor constituted of one or two Ig like domains or of one or two fibronectin III domains. If necessary, the TYRO3 receptor domains may be coupled with a Fc Fragment to stabilize the receptor.

In a particular embodiment, the TYRO3 soluble bait is able to bind to Gas6 and/or protein S.

In another particular embodiment, the TYRO3 soluble bait is an antibody directed against Gas6 and/or protein S, preferably against Gas6. Gas6 and the protein S have been described to activate TYRO3 tyrosine kinase activity. For example, antibodies against Gas6 may be one of the following antibodies or a chimeric, humanized or human derivatives thereof : monoclonal antibody CNTO300 (Fisher et al., 2005), blocking anti-human GAS6 sc1935 (Gould et al., 2005), neutralizing polyclonal gas6 antibody (Stenhoff et al.,2004), and other commercially available anti-Gas6 antibodies (Santa Cruz Biotechnology: catalogue number: sc-1935, sc-22759, sc-74035, sc-1936, sc-16660; R&D Systems: catalogue ref: MAB885 and AF885; Novus Biologicals: catalogue ref: H00002621-D01P, NBP1-00843, H00002621-A01, H00002621-B01; IBL—America (Immuno-Biological Laboratories): catalogue ref BW02563; Bioworld Technology: catalogue number: BS2563; Atlas Antibodies: catalogue number: HPA008275; Acris Antibodies GmbH: catalogue number: AP01178PU-N; Abcam: catalogue number: ab67099; and Sigma Aldrich: catalogue number:HPA008275).

The inhibitors of TYRO3 tyrosine kinase of the invention may also be nucleic acid molecules. The terme "nucleic acid molecule" includes, but is not limited to, RNAi, antisense and ribozyme molecules.

In the present invention, a "nucleic acid molecule specifically interfering with TYRO3 expression" is a nucleic acid molecule which is able to reduce or to suppress the expression of gene coding for TYRO3 receptor, in a specific way.

The term "RNAi" or "interfering RNA" means any RNA which is capable of down-regulating the expression of the targeted protein. It encompasses small interfering RNA (siRNA), double-stranded RNA (dsRNA), single-stranded RNA (ssRNA), micro-RNA (miRNA), and short hairpin RNA (shRNA) molecules. RNA interference, designate a phenomenon by which dsRNA specifically suppresses expression of a target gene at post-translational level. In normal conditions, RNA interference is initiated by double-stranded RNA molecules (dsRNA) of several thousands of base pair length. In vivo, dsRNA introduced into a cell is cleaved into a mixture of short dsRNA molecules called siRNA. The enzyme that catalyzes the cleavage, Dicer, is an endo-RNase that contains RNase III domains (Bernstein, Caudy et al. 2001). In mammalian cells, the siRNAs produced by Dicer are 21-23 by in length, with a 19 or 20 nucleotides duplex sequence, two-nucleotide 3' overhangs and 5'-triphosphate extremities (Zamore, Tuschl et al. 2000; Elbashir, Lendeckel et al. 2001; Elbashir, Martinez et al. 2001).

A number of patents and patent applications have described, in general terms, the use of siRNA molecules to inhibit gene expression, for example, WO 99/32619, US 20040053876, US 20040102408 and WO 2004/007718.

siRNA are usually designed against a region 50-100 nucleotides downstream the translation initiator codon, whereas 5'UTR (untranslated region) and 3'UTR are usually avoided. The chosen siRNA target sequence should be subjected to a BLAST search against EST database to ensure that the only desired gene is targeted. Various products are commercially available to aid in the preparation and use of siRNA.

In a preferred embodiment, the RNAi molecule is a siRNA of at least about 15-50 nucleotides in length, preferably about 20-30 base nucleotides, preferably about 20-25 nucleotides in length.

In a particular embodiment, the siRNA molecule comprises the sequence of SEQ ID No. 1.

RNAi can comprise naturally occurring RNA, synthetic RNA, or recombinantly produced RNA, as well as altered RNA that differs from naturally-occurring RNA by the addition, deletion, substitution and/or alteration of one or more nucleotides. Such alterations can include addition of non-nucleotide material, such as to the end of the molecule or to one or more internal nucleotides of the RNAi, including modifications that make the RNAi resistant to nuclease digestion.

RNAi may be administered in free (naked) form or by the use of delivery systems that enhance stability and/or targeting, e.g., liposomes, or incorporated into other vehicles, such as hydrogels, cyclodextrins, biodegradable nanocapsules, bioadhesive microspheres, or proteinaceous vectors (WO 00/53722), or in combination with a cationic peptide (US 2007275923). They may also be administered in the form of their precursors or encoding DNAs.

In a particular embodiment, RNAi are encapsulated within vesicles, preferably within liposomes.

Antisense nucleic acid can also be used to down-regulate the expression of the TYRO3 receptor. The antisense nucleic acid can be complementary to all or part of a sense nucleic acid encoding a TYRO3 receptor polypeptide e.g., complementary to the coding strand of a double-stranded cDNA molecule or complementary to an mRNA sequence, and it thought to interfere with the translation of the target mRNA In a preferred embodiment, the antisense nucleic acid is a RNA molecule complementary to a target mRNA encoding a TYRO3 receptor polypeptide.

An antisense nucleic acid can be, for example, about 5, 10, 15, 20, 25, 30, 35, 40, 45 or 50 nucleotides in length. Particularly, antisense RNA molecules are usually 18-50 nucleotides in length.

An antisense nucleic acid for use in the method of the invention can be constructed using chemical synthesis and enzymatic ligation reactions using procedures known in the art. Particularly, antisense RNA can be chemically synthesized, produced by in vitro transcription from linear (e.g. PCR products) or circular templates (e.g., viral or non-viral vectors), or produced by in vivo transcription from viral or non-viral vectors.

Antisense nucleic acid may be modified to have enhanced stability, nuclease resistance, target specificity and improved pharmacological properties. For example, antisense nucleic acid may include modified nucleotides designed to increase the physical stability of the duplex formed between the antisense and sense nucleic acids, e.g., phosphorothioate derivatives and acridine substituted nucleotides.

Ribozyme molecules can also be used to decrease levels of functional TYRO3 tyrosine kinase. Ribozymes are catalytic RNA molecules with ribonuclease activity which are capable of cleaving a single-stranded nucleic acid, such as an mRNA, to which they have a complementary region. Thus, ribozymes can be used to catalytically cleave mRNA transcripts to thereby inhibit translation of the protein encoded by the mRNA. Ribozyme molecules specific for functional TYRO3 tyrosine kinase can be designed, produced, and administered by methods commonly known to the art (see e.g., Fanning and Symonds, 2006, reviewing therapeutic use of hammerhead ribozymes and small hairpin RNA).

The term "cancer" or "tumor", as used herein, refers to the presence of cells possessing characteristics typical of cancer-causing cells, such as uncontrolled proliferation, immortality, metastatic potential, and certain characteristic morphological features. This term refers to any type of malignancy (primary or metastases).

The term "TYRO3 over-expressing cancer" as used herein, refers to any type of cancer or tumor in which TYRO3 is upregulated. The expression level of TYRO3 can be determined from a cancer sample by a variety of techniques well-known by the skilled person. The expression level of TYRO3 can be determined by measuring the quantity of TYRO3 protein or TYRO3 mRNA or by assessing the TYRO3 activity. The TYRO3 expression can be assayed by quantitative RT-PCR or using any method known by the man skilled in the art. The TYRO3 expression in the tumor tissue should be compared to the expression in normal proliferative cell lines, preferably to normal cells providing from the same tissue than the tumor. In a particular embodiment, the TYRO3 over-expressing cancer is selected from the group consisting of bladder tumor, diffuse large B-Cell lymphoma, adenoid cystic carcinoma of salivary gland, Burkitt lymphoma, multiple myeloma, pancreatic ductal adenocarcinoma, hairy cell leukemia, metastactic prostate cancer, melanoma and colorectal cancer. In a preferred embodiment, the TYRO3 over-expressing cancer is a bladder tumor.

By "bladder tumor" is intended herein urinary bladder tumor, bladder cancer or urinary bladder cancer, and bladder neoplasm or urinary bladder neoplasm. A bladder tumor can be a bladder carcinoma or a bladder adenoma. The most common staging system for bladder tumors is the TNM (tumor, node, metastasis) system. This staging system takes into account how deep the tumor has grown into the bladder, whether there is cancer in the lymph nodes and whether the cancer has spread to any other part of the body. In a preferred embodiment, the bladder tumor is a bladder carcinoma. In a preferred embodiment, the bladder carcinoma to be treated is a T stage. In addition, the bladder carcinomas of T stage can have sub-stages:

CIS—very early cancer cells are detected only in the innermost layer of the bladder lining;
Ta—the cancer is just in the innermost layer of the bladder lining;
T1—the cancer has started to grow into the connective tissue beneath the bladder lining;
T2—the cancer has grown through the connective tissue into the muscle;
T2a—the cancer has grown into the superficial muscle;
T2b—the cancer has grown into the deeper muscle;
T3—the cancer has grown through the muscle into the fat layer;
T3a—the cancer in the fat layer can only be seen under a microscope;
T3b—the cancer in the fat layer can be seen on tests, or felt by the physisian;
T4—the cancer has spread outside the bladder;
T4a—the cancer has spread to the prostate, womb or vagina;
T4b—the cancer has spread to the wall of the pelvis and abdomen.

Accordingly, the bladder tumor or carcinoma that can be treated by the present invention can be superficial (Ta, T1) or invasive (T2 to T4). In a particular embodiment, the bladder carcinoma that can be treated by the present invention can be any and all T sub-stages.

In a preferred embodiment, a sample from the subject to be treated, in particular a bladder tumor sample, is assayed for the overexpression of TYRO3. Accordingly, the treatment with the TYRO3 inhibitor is more particularly appropriate for a subject having a tumor overexpressing TYRO3, in particular a bladder tumor overexpressing TYRO3.

As used herein, the term "treatment" of a disease refers to any act intended to extend life span of patients such as therapy and retardation of the disease. The treatment can be designed to eradicate the tumor, to stop the progression of the tumor, to prevent the occurence of metastasis, to promote the regression of the tumor and/or to prevent muscle invasion of cancer. The patient to treat is any mammal, preferably a human being.

The treatment of TYRO3 over-expressing cancer with pharmaceutical composition according to the invention can be associated with other therapy such as surgery, radiation therapy or other chemotherapy.

By a "therapeutically efficient amount" is intended an amount of therapeutic agent, an inhibitor of TYRO3 tyrosine kinase, administered to a patient that is sufficient to constitute a treatment of TYRO3 over-expressing cancer as defined above.

The pharmaceutical composition comprising the inhibitor of TYRO3 tyrosine kinase is formulated in accordance with standard pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York) known by a person skilled in the art.

Possible pharmaceutical compositions include those suitable for oral, rectal, intravesial, topical (including transdermal, buccal and sublingual), or parenteral (including subcutaneous, intramuscular, intravenous and intradermal) administration.

For these formulations, conventional excipient can be used according to techniques well known by those skilled in the art.

The compositions for parenteral administration are generally physiologically compatible sterile solutions or suspensions which can optionally be prepared immediately before use from solid or lyophilized form. Adjuvants such as a local anesthetic, preservative and buffering agents can be dissolved in the vehicle and a surfactant or wetting agent can be included in the composition to facilitate uniform distribution of the active ingredient.

For oral administration, the composition can be formulated into conventional oral dosage forms such as tablets, capsules, powders, granules and liquid preparations such as syrups, elixirs, and concentrated drops. Non toxic solid carriers or diluents may be used which include, for example, pharmaceutical grades of mannitol, lactose, starch, magnesium stearate, sodium saccharine, talcum, cellulose, glucose, sucrose, magnesium, carbonate, and the like. For compressed tablets, binders, which are agents which impart cohesive qualities to powdered materials, are also necessary. For example, starch, gelatine, sugars such as lactose or dextrose, and natural or synthetic gums can be used as binders. Disintegrants are also necessary in the tablets to facilitate break-up of the tablet. Disintegrants include starches, clays, celluloses, algins, gums and crosslinked polymers. Moreover, lubricants and glidants are also included in the tablets to prevent adhesion to the tablet material to surfaces in the manufacturing process and to improve the flow characteristics of the powder material during manufacture. Colloidal silicon dioxide is most commonly used as a glidant and compounds such as talc or stearic acids are most commonly used as lubricants.

For transdermal administration, the composition can be formulated into ointment, cream or gel form and appropriate penetrants or detergents could be used to facilitate permeation, such as dimethyl sulfoxide, dimethyl acetamide and dimethylformamide.

For transmucosal administration, nasal sprays, rectal or vaginal suppositories can be used. The active compound can be incorporated into any of the known suppository bases by methods known in the art. Examples of such bases include cocoa butter, polyethylene glycols (carbowaxes), polyethylene sorbitan monostearate, and mixtures of these with other compatible materials to modify the melting point or dissolution rate.

Pharmaceutical compositions according to the invention may be formulated to release the active drug substantially immediately upon administration or at any predetermined time or time period after administration.

Pharmaceutical compositions according to the invention can comprise one or more TYRO3 tyrosine kinase inhibitor (s) associated with pharmaceutically acceptable excipients and/or carriers. These excipients and/or carriers are chosen according to the form of administration as described above. Other active compounds can also be associated with TYRO3 tyrosine kinase inhibitors, in particular antitumoral drugs such as tamoxifen, aromatase inhibitors, trastuzumab, GnRH-analogues, gemcitabine, docetaxel, paclitaxel, mitomycin, cisplatin, carboplatin, oxaliplatin, doxorubicin, daunorubicin, docetaxel, cyclophosphamide, epirubicin, fluorouracil, methotrexate, mitozantrone, vinblastine, vincristine, vinorelbine, bleomycin, estramustine phosphate or etoposide phosphate. In a particular embodiment, TYRO3 tyrosine kinase inhibitors may be associated with other molecules used for the treatment of bladder cancer (e.g. cisplatin, adriamycin, mitomycin C, gemcitabine, paclitaxel or docetaxel).

In a particular embodiment, the pharmaceutical composition comprises one or more inhibitor(s) of the TYRO3 tyrosine kinase selected from the group consisting of a small molecule inhibiting the tyrosine kinase activity, an antibody directed against the extracellular domain of TYRO3, a RNAi molecule specific of TYRO3, particularly a siRNA, a dominant negative receptor presenting a kinase dead domain, an antibody directed against Gas6 and a TYRO3 soluble receptor.

In a preferred embodiment, the pharmaceutical composition comprises one or more inhibitor(s) of the TYRO3 tyrosine kinase selected from the group consisting of an antibody directed against the extracellular domain of TYRO3, a RNAi molecule specific of TYRO3, particularly a siRNA, a dominant negative receptor presenting a kinase dead domain, an antibody directed against Gas6 and a TYRO3 soluble receptor.

The amount of inhibitor of TYRO3 tyrosine kinase to be administered has to be determined by standard procedure well known by those of ordinary skill in the art. Physiological data of the patient (e.g. age, size, and weight), the routes of administration and the disease to be treated have to be taken into account to determine the appropriate dosage.

The inhibitor of TYRO3 tyrosine kinase may be administered as a single dose or in multiple doses. If the inhibitor of TYRO3 tyrosine kinase is a small molecule inhibiting the tyrosine kinase activity, each unit dosage may contain, for example, from 200 to 1000 mg/kg of body weight, particularly from 500 to 800 mg/kg of body weight. If the inhibitor of TYRO3 tyrosine kinase is an antibody directed against the extracellular domain of TYRO3, each unit dosage may contain, for example, from 0.1 to 20 mg/kg of body weight, particularly from 4 to 10 mg/kg of body weight. If the inhibitor of TYRO3 tyrosine kinase is a RNAi molecule specific of TYRO3, each unit dosage may contain, for example, from 2 to 50 mg/kg of body weight, particularly from 5 to 20 mg/kg of body weight. If the inhibitor of TYRO3 tyrosine kinase is a dominant negative receptor presenting a kinase dead domain or a TYRO3 soluble receptor, each unit dosage may contain, for example, from 5 to 100 mg/kg of body weight, particularly from 15 to 70 mg/kg of body weight. If the inhibitor is an antibody directed against Gas6 or the protein S, each unit dosage may contain, for example, from 0.1 to 20 mg/kg of body weight, particularly from 4 to 10 mg/kg of body weight.

TYRO3 inhibitor can be used in combination with other active ingredients, in particular, other TYRO3 inhibitors or with other treatments of cancer such as tamoxifen, aromatase inhibitors, trastuzumab, GnRH-analogues, gemcitabine, docetaxel, paclitaxel, mitomycin, cisplatin, carboplatin, oxaliplatin, doxorubicin, daunorubicin, docetaxel, cyclophosphamide, epirubicin, fluorouracil, methotrexate, mitozantrone, vinblastine, vincristine, vinorelbine, bleomycin, estramustine phosphate or etoposide phosphate. In particular, TYRO3 inhibitor can be used in combination with other treatments of bladder cancer, such as BCG treatment (e.g. WO05/077411) or administration of anticancer drugs, for example cisplatin, adriamycin, mitomycin C, gemcitabine, paclitaxel or docetaxel. In this case, TYRO3 inhibitors and the other molecules can be administered simultaneously or consecutively.

The present invention further provides a method for treating a TYRO3 over-expressing cancer in a subject comprising administering a therapeutically efficient amount of a TYRO3 tyrosine kinase inhibitor to the subject. In a particular embodiment, the TYRO3 over-expressing cancer is selected from the group consisting of bladder tumor, diffuse large B-Cell lymphoma, adenoid cystic carcinoma of salivary gland, Burkitt lymphoma, multiple myeloma, pancreatic ductal adenocarcinoma, hairy cell leukemia, metastactic prostate cancer, melanoma and colorectal cancer. In a preferred embodiment, the TYRO3 over-expressing cancer is a bladder tumor. Preferably, the subject is a human.

The present invention also concerns the use of a TYRO3 tyrosine kinase inhibitor for the preparation of a medicament for the treatment of a TYRO3 over-expressing cancer.

The present invention provides a method for screening or identifying a molecule suitable for treating a TYRO3 over-expressing cancer. The method may be in vivo, ex vivo or in vitro method, preferably in vitro method.

In a particular embodiment, the TYRO3 over-expressing cancer is selected from the group consisting of bladder tumor, diffuse large B-Cell lymphoma, adenoid cystic carcinoma of salivary gland, Burkitt lymphoma, multiple myeloma, pancreatic ductal adenocarcinoma, hairy cell leukemia, metastactic prostate cancer, melanoma and colorectal cancer. In a preferred embodiment, the TYRO3 over-expressing cancer is a bladder tumor.

This method is based on the analysis of the ability of a molecule to bind to TYRO3 receptor, to compete with or for a ligand of TYRO3 receptor, to decrease the TYRO3 gene expression or to decrease the phosphorylation of the TYRO3 substrates or the TYRO3 autophosphorylation.

In one embodiment, the method for screening or identifying a molecule suitable for treating a TYRO3 over-expressing cancer comprises the steps of (i) contacting candidate molecules with TYRO3 receptor, and (ii) selecting molecules having the ability to bind to TYRO3 receptor and/or to compete with and/or for a ligand of TYRO3 receptor and/or to decrease the phosphorylation of the TYRO3 substrates or the TYRO3 autophosphorylation. The method can comprise a step (i') of determining the ability of candidate molecules to bind to TYRO3 receptor and/or to compete with and/or for a ligand of TYRO3 receptor and/or to decrease the phosphorylation of the TYRO3 substrates or the TYRO3 autophosphorylation.

In an other embodiment, the method for screening or identifying a molecule suitable for treating a TYRO3 over-expressing cancer comprises the steps of (i) contacting candidate molecules with cells expressing TYRO3 receptor, and (ii) selecting molecules having the ability to bind to TYRO3 receptor and/or to compete with and/or for a ligand of TYRO3 receptor and/or to decrease the TYRO3 gene expression and/or to decrease the phosphorylation of the TYRO3 substrates or the TYRO3 autophosphorylation. Cells used for this screening can be cells expressing high level of endogenous TYRO3, such as most of bladder cell lines, in particular J82 or RT112 cell lines, or genetically modified cells over-expressing TYRO3 allowing an optimized detection of tyrosine kinase activity. The method can comprise a step (i') of determining the ability of candidate molecules to bind to TYRO3 receptor and/or to compete with and/or for a ligand of TYRO3 receptor and/or to decrease the phosphorylation of the TYRO3 substrates or the TYRO3 autophosphorylation.

The binding of a molecule to TYRO3 receptor can be measured by well-known techniques such as surface plasmon resonance, calorimetry or Biacore technology.

The ability of a molecule to compete with or for a ligand of TYRO3 receptor can be evaluated, for example, by competition experiments with labelled ligand, in particular radio-labelled ligand, Biacore or spectroscopic observations.

The TYRO3 gene expression can be evaluated with different well known techniques, such as quantitative RT-PCR, Northern-blot, ELISA or Western-blot.

The TYRO3 phosphorylation level can be assessed by western-blot using an anti-phosphotyrosine or an anti-phospho-TYRO3 antibody, radioactive FlashPlate assay, fluorescent resonance energy transfer (FRET) assay or dissociation-enhance lanthanide fluorescence immunoassay (DELFIA).

This method as described above can further comprise a subsequent step consisting of administering molecule previously selected by the in vitro method of the invention as disclosed above, in a TYRO3 over-expressing cancer non human animal model, in particular in a bladder tumor non human animal model, and analyzing the effect on the tumor progression. The efficiency of the molecule can be evaluated, for instance, by analyzing the life span of animals, the occurrence of metastasis, the progression of the tumor, the occurrence of muscle invasion of cancer. All these characteristics have to be compared with those of controls consisting of TYRO3 over-expressing cancer non human animal models, such as bladder tumor non human animal model, with no treatment. The non human animal model may be nude mice with grafted tumor. In a particular embodiment, the grafter tumor is a bladder tumor.

The following examples are given for purposes of illustration and not by way of limitation.

EXAMPLES

Example 1

TYRO-3 and GAS6 Over-Expression in Bladder Tumors

RNA levels were analyzed using Affymetrix DNA microarrays U95A in 80 bladder carcinomas, 5 normal bladder urothelium. SAM software (http://www-stat.stanford-.edu/~tibs/SAM) was used to identify genes displaying differential expression between tumoral and normal samples. SAM with the parameters "false discovery rate of 10%" and "SAM fold change of at least 2" identified 823 probe sets significantly more strongly expressed in tumors as compared to normal urothelium and 477 probe sets less strongly expressed in tumors.

Figure 1A:
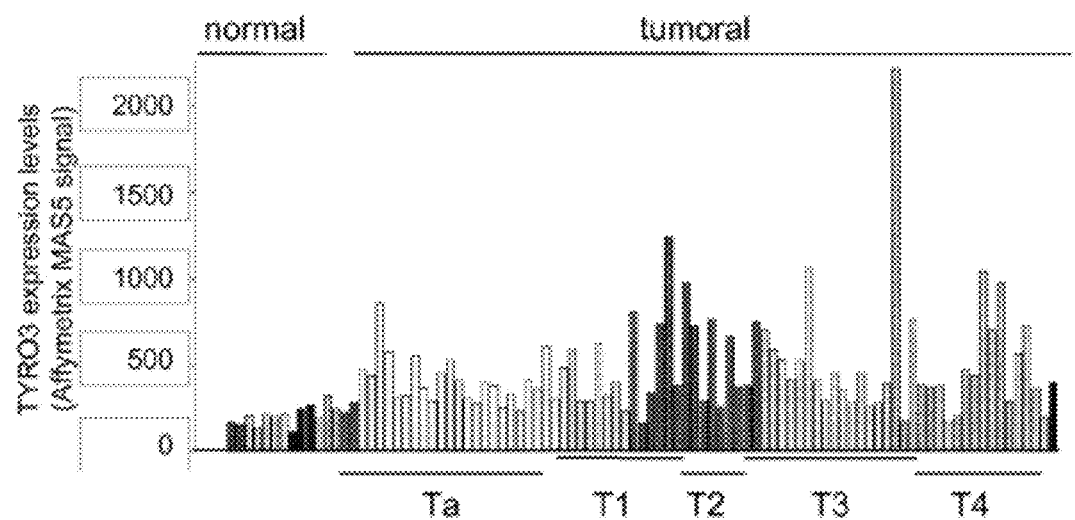
FIG. 1 shows TYRO3 expression in bladder tumors and bladder cancer cell lines. mRNA expression levels in human bladder cancer tumors were assessed using Affymetrix U95A DNA microarray (FIG. 1A). The difference in expression between different groups were compared using an ANOVA test (FIG. 1B)
Figure 1B:
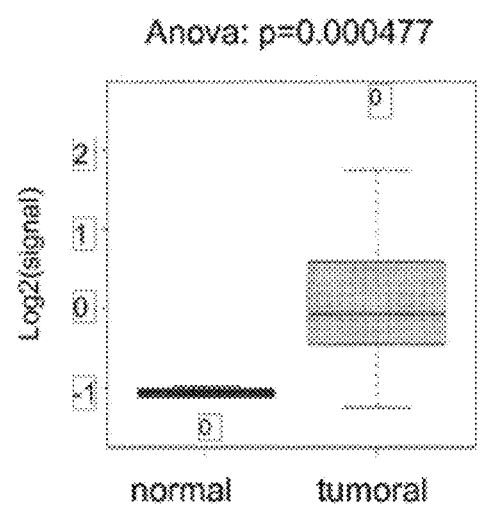

Among these up-regulated genes, TYRO-3 kinase was focused and the results obtained with SAM were confirmed using an ANNOVA test (FIG. 1B). The level of TYRO3 RNA (MAS 5 Affymetrix DNA chips data) in each tumor sample was then compared with the distribution of TYRO3 RNA levels in normal samples and the difference was considered significant if it exceeded three standard deviations (z-score>3, $p<0.0013$). TYRO3 was significantly over-expressed in 57/80 tumors (71%). This over-expression was independent of tumor stage and grade (FIG. 1A). These results obtained from Affymetrix data were confirmed by Q-RT-PCR analysis (data not shown).

Figure 2A:
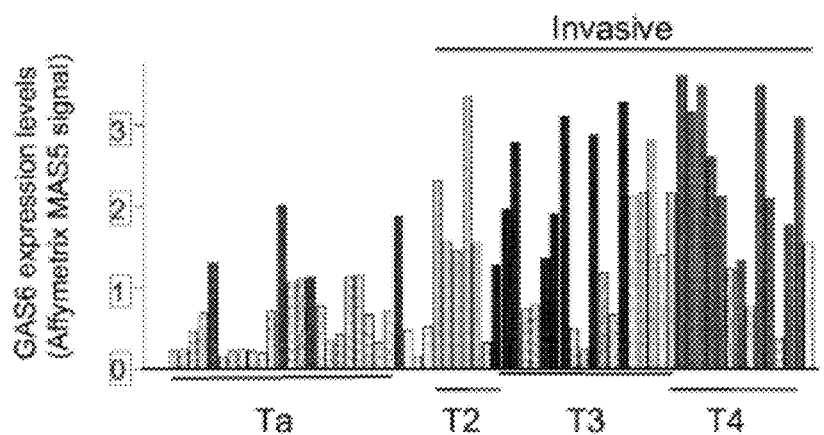
FIG. 2 shows GAS6 expression in bladder tumors and bladder cancer cell lines. mRNA expression levels in human bladder cancer tumors were assessed using Affymetrix U95A DNA microarray (FIG. 2A) and the difference in expression between different groups were compared using an ANOVA test (FIG. 2B)
Figure 2B:
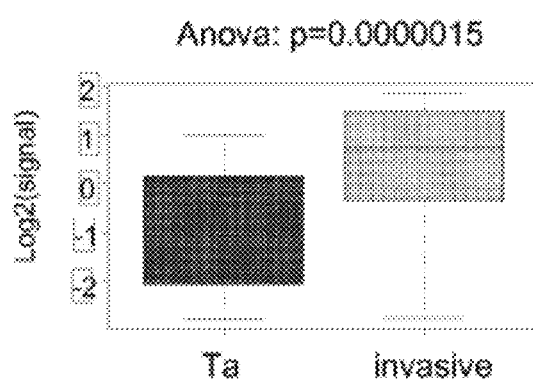

Interestingly, GAS6, the only known ligand of TYRO3, was also significantly over-expressed in invasive tumors as compared to normal or superficial tumors (SAM analysis of differentially expressed genes between normal and invasive samples or superficial and invasive tumors, confirmed by ANNOVA test) (FIG. 2A).

No correlation between mRNA expression level and DNA copy number at the TYRO3 OR GAS6 locus was observed suggesting that TYRO3 and GAS6 over-expression were not due do DNA amplification. In situ hybridization showed that TYRO3 was expressed by epithelial cells whereas GAS6 is expressed by both epithelial and stromal cells suggesting hence a possible autocrine or paracrine activation of TYRO3 by GAS6 in invasive tumors and hence a reinforcement of TYRO3 role in those carcinomas (data not shown). No mutation of TYRO3 was found in a subset of 15 bladder tumor samples expressing various levels of TYRO3 mRNA.

Example 2

Effect of Inhibition of TYRO3 Activity in Bladder Tumor Cells

Figure 3:
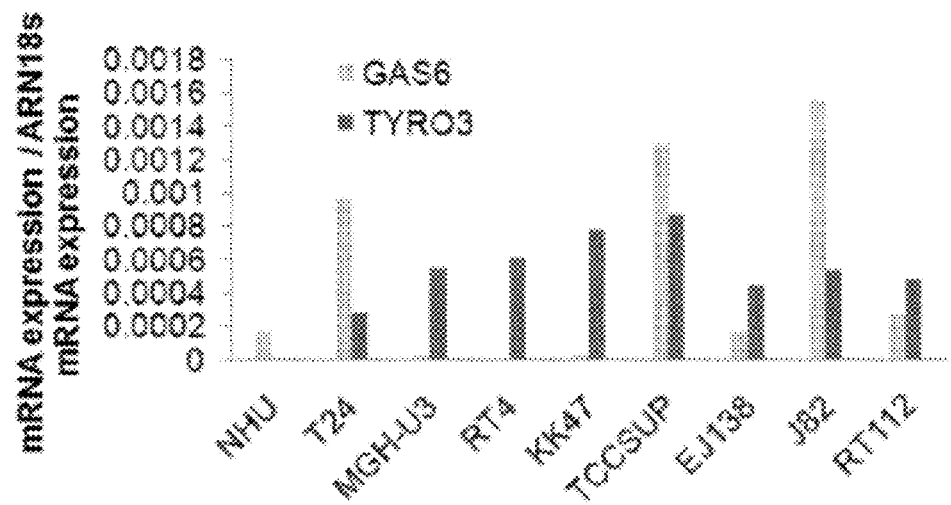
FIG. 3 shows TYRO3 and GAS6 mRNA expression levels in human bladder cancer cell lines T24, MGH-U3, RT4, KK47, TCCSUP, EJ138, J82 and RT112 and in NHU normal urothelium derived cell line assessed by Q-RT-PCR.

To explore the role of TYRO3 in bladder carcinoma, the first step was to identify bladder cancer derived cell lines mimicking superficial tumors expressing only TYRO3 and invasive tumors expressing both TYRO3 and GAS6. TYRO3 and GAS6 mRNA expression levels were therefore investigated in 8 bladder cancer derived cell lines (T24, RT4, KK47, TCCSUP, EJ138, J82 and RT112 cell lines (ATCC) and MGH-U3 cell line (Lin et al., 1985)) and in one normal urothelium derived cell line, NHU (ATCC), by Q-RT-PCR (FIG. 3). All studied tumor cell lines expressed more strongly TYRO3 as compared to the normal proliferative cell line, suggesting that TYRO3 expression was cancer dependent and not linked to cell proliferation.

In order to investigate the role of TYRO3 in cell growth and tumorigenic properties, TYRO3 expression was blocked using RNA interference technology or TYRO3 activity was inhibited using a blocking antibody directed against the extracellular domain of TYRO3 or a soluble receptor consisting of the recombinant extracellular domain of TYRO3 produced in bacteria. Two cell lines expressing TYRO3 (MGH-U3, KK47), two cell lines expressing both TYRO3 and GAS6 (J82, RT112) and one control breast cancer derived cell line presenting a very low TYRO3 expression level (MCF-7) were used. It was shown by western blot using an anti-phosphotyrosine antibody after TYRO3 immunoprecipitation that in each type of cell line (expressing or not GAS6), TYRO was activated (data not shown).

Figure 4:
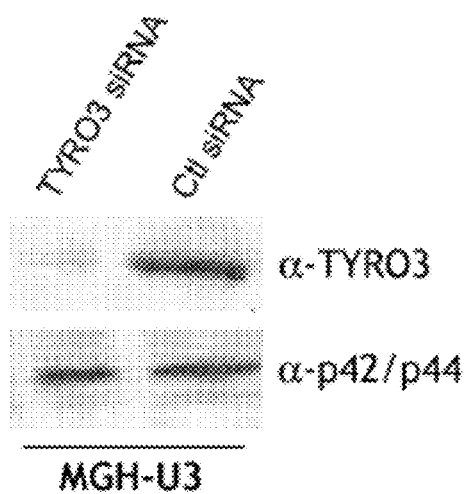
FIG. 4 shows the efficiency of TYRO3 silencing in MGH-U3 cells. Cells were transfected with 50 nM siRNA (siRNA anti-TYRO3 (SEQ ID No. 1) or control siRNA (scramble, SEQ ID No. 2)) and the efficiency of TYRO3 silencing was assessed 72 hours after transfection by western-blot.
Figure 5:
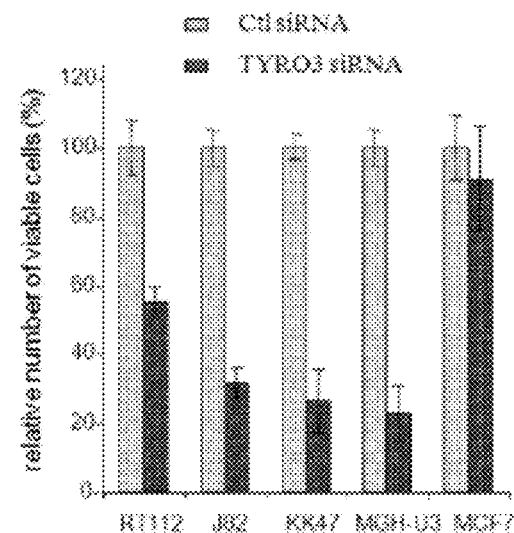
FIG. 5 shows a graph representing the effect of TYRO3 knockdown on bladder cancer cell viability. After transfection as described in the legend of FIG. 4, cells were treated with trypsin 72 hours after transfection, stained with trypan blue and viable cells were counted in triplicate, using a Malassez hematocytometer. Results are the means+/−SD of two independent experiments carried out in triplicate.
Figure 6:
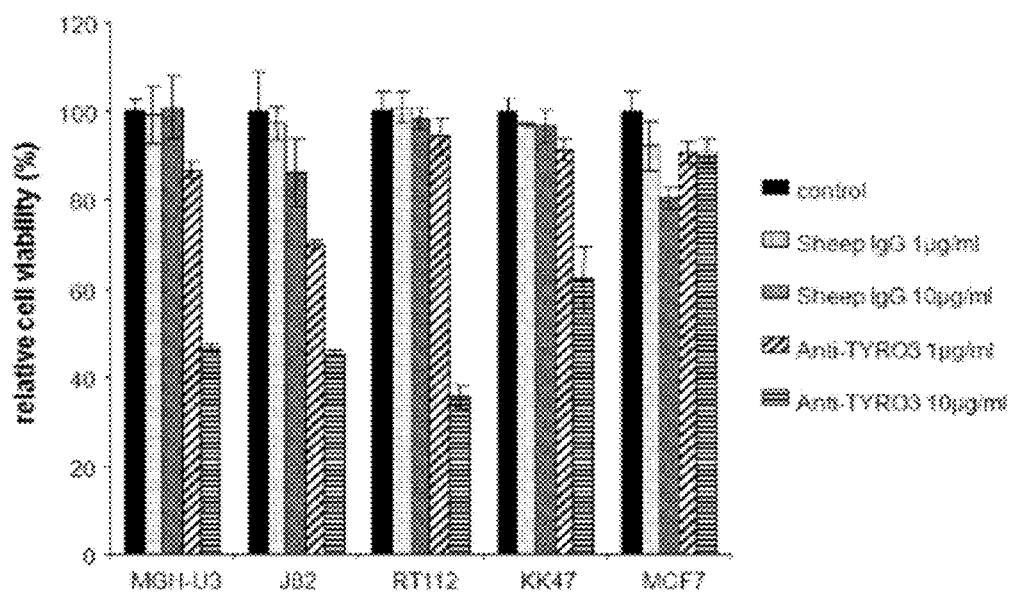
FIG. 6 shows the effect of TYRO3 antibody on bladder cancer cell viability.

The transfection of MGH-U3, KK47, J82 and RT112 cells with TYRO3 siRNAs markedly decreased TYRO3 mRNA and protein levels (80-90% inhibition) (Results for MGH-U3 cells are presented FIG. 4). This knockdown of TYRO3 yielded fewer viable MGH-U3, KK47, J82 and RT112 cells than the control siRNA (FIG. 5) whereas it had no effect on MCF7 cells, suggesting that the effect observed following transfection with the specific siRNA was rather due to a specific gene silencing than to an off-target effect. The same effect on cell growth was also obtained by blocking TYRO3 using a polyclonal antibodies directed against its extra-cellular domain (FIG. 6) or a recombinant soluble receptor consisting of the entire extracellular domain of TYRO3 (aa 1 to 421) (FIG. 7).

This decreased number of viable cells could be attributed to an increased apoptotic rate (FIG. 8) with significant but low change in cell-cycle progression (FIG. 9). TYRO3 knockdown also yielded fewer viable MGH-U3, KK47, RT112 and J82 colonies in soft agar assays demonstrating that TYRO3 regulated cell survival of clonogenic cancer cells (FIG. 10).

Example 3

In vivo Studies of the Role of TYRO3 in Bladder Cancer Cell Growth

Hence our results clearly demonstrated that TYRO3 regulate bladder cancer cells survival/proliferation in vitro. The role of this gene in bladder cancer cell growth in vivo was studied. J82 and MGH-U3 cells were implanted subcutaneously in athymic nude mice. Once tumors were established, mice were randomly selected for treatment with control or TYRO3-specific siRNAs. For J82 xenografts, two weeks after the beginning of treatment only three tumors out of 12 were still observed (FIGS. 11A and 11B). For MGH-U3 xenografts, after 21 days of treatment, tumor volume was 70% lower in mice treated with TYRO3 siRNA than in mice treated with control siRNA (Wilcoxon rank-sum test, p<0.001) (FIGS. 12A and 12B).

This inhibition of tumor growth was associated with a significant decrease in TYRO3 mRNA levels (Student's t-test, p<0,001) measured at a time (3 days after the last siRNA injection) where this decrease should be the lowest one (FIG. 13). No histological difference was observed between treated and control tumors (data not shown), but TUNNEL analysis demonstrated that tumor growth inhibition was due to increase apoptosis in treated tumors (data not shown).

The ability of a soluble receptor consisting of the recombinant extracellular domain of TYRO3 produced in bacteria to induce bladder cancer cell growth inhibition was also tested in vivo. MGH-U3 cells were implanted subcutaneously in athymic nude mice.

Once tumors were established, mice were randomly selected for treatment with PBS or TYRO3-soluble receptor. After 18 days of treatment, tumor volume was 70% lower in mice treated with TYRO3 soluble receptor than in mice treated with PBS (Wilcoxon rank-sum test, p<0.001) (FIGS. 14A and 14B). This inhibition of tumor growth was due to increase apoptosis in treated tumors (FIG. 15).

Taken together our results identified TYRO3 as a major gene implicated in bladder carcinoma being up-regulated in the majority of cases (70-75% of tumors) independently of tumors stage and/or grade and being responsible for tumor cell survival. Furthermore, these experiments demonstrate that compounds inducing inhibition or depletion of TYRO3 provoke an enhanced apoptosis of bladder tumor cells and, consequently, can be used to treat bladder tumor.

Example 4

TYRO3 Over-expression in Several Types of Tumors

Since TYRO3 over-expression was identified in bladder tumors and the anti-apoptotic role of TYRO3 was demonstrated in this context, the inventors wondered whether TYRO3 could be involved in other cancers and consequently could be used as a therapeutic target to treat those tumors. Using publicly available data compiled in the Oncomine website, 7 types of cancers where TYRO3 was upregulated in tumors, as compared to normal samples, were identified: Bladder carcinoma, Diffuse Large B-Cell Lymphoma, Adenoid Cystic Carcinoma Of Salivary Gland, Burkitt Lymphoma, Multiple Myeloma, Pancreatic Ductal Adenocarcinoma and hairy Cell Leukemia (FIGS. 16A and 16B). The inventors also identified another cancer, prostate, where TYRO3 expression increased during tumor progression, i.e. in metastactic prostate cancers, as compared to prostate carcinoma (data not shown). Using GeneSapiens database to obtain plots of TYRO3 expression in a large spectrum of normal (FIG. 17) and tumoral tissues (FIG. 18), TYRO3 over-expression was also identified in two other cancer types: melanoma and colorectal cancer.

References

Abbas-Terki, T., et al. (2002). *Hum Gene Ther* 13(18): 2197-201.
An, D. S., et al. (2003). *Hum Gene Ther* 14(12): 1207-12.
Bernstein, E., et al. (2001). *Nature* 409(6818): 363-6.
Bridge, A. J., et al. (2003). *Nat Genet* 34(3): 263-4.
Elbashir, S. M., et al. (2001). *Embo J* 20(23): 6877-88.
Elbashir, S. M., et al. (2001). *Genes Dev* 15(2): 188-200.

Fanning and Symonds (2006) *RNA Towards Medicine* (*Handbook of Experimental Pharmacology*), ed. Springer p. 289-303
Fisher et al., 2005, *Biochem J.* 3: 727-735.
Gould et al., 2005, *J Thromb Haemost.* 4:733-741
Harlow, E. and Lane, D. (1988) *Antibodies: A Laboratory Manual*, ed., Cold Spring Harbor Laboratory.
Karaman M, et al. (2008) *Nat Biotechnol* 26(1): 127-32.
Lai C, et al. *Oncogene.* (1994) 9, 2567-2578.
Lan Z, et al. *Blood.* (2000) 2, 633-8.
Lin, C. W. et al. (1985) *Cancer Res.,* 45(10): 5070-5079
Scherr, M., et al. (2003). *Cell Cycle* 2(3): 251-7.
Stenhoff et al., 2004, *Biochem Biophys Res Commun.* 3: 871-878
Sun W S, et al. *Mol Hum Reprod.* (2002) 8,552-558.
Sun W S, et al. *Mol Hum Reprod.* (2003a) 11,701-707.
Sun W S, et al. *Ann Oncol.* (2003b) 6, 898-906.
Taylor I C, et al. (1995) *J. Biol. Chem.* 270, 6872-6880.
Xia, H., et al. (2002). *Nat Biotechnol* 20(10): 1006-10.
Wimmel A, et al. *Cancer.* (1999) 1, 43-49.
Zamore, P. D., et al. (2000). *Cell* 101(1): 25-33.
Rhodes et al. (2004) *Neoplasia* 6(1):1-6.
Kilpinen et al., (2008) *Genome Biology* 9(9):R139 against the extracellular domain of TYRO3, a nucleic acid molecule interfering specifically with TYRO3 expression, a dominant negative receptor TYRO3 presenting a kinase dead domain and a TYRO3 soluble bait.

3. The method according to claim 2, wherein the nucleic acid molecule interfering specifically with TYRO3 expression is a RNAi, an antisense nucleic acid or a ribozyme.

4. The method according to claim 3, wherein the RNAi is a siRNA.

5. The method according to claim 2, wherein the TYRO3 soluble bait is a recombinant TYRO3 receptor comprising at least one Ig-like or fibronectin III domain of the extracellular domain of the receptor.

6. The method according to claim 2, wherein the TYRO3 soluble bait is an antibody directed against Gas6 and/or protein S.

7. The method according to claim 1, wherein the inhibitor of TYRO3 tyrosine kinase is used in combination with a second active ingredient.

8. The method according to claim 4, wherein the siRNA comprises the sequence of SEQ ID NO: 1.

9. The method according to claim 7, wherein the second active ingredient is an antitumoral drug.

The invention claimed is:

1. A method for treating a subject having a TYRO3 over-expressing cancer
comprising administering a therapeutically effective amount of a composition comprising a TYRO3 inhibitor to a subject having a cancer that overexpresses TYRO3 tyrosine kinase, wherein the TYRO3 over-expressing cancer is selected from the group consisting of bladder cancer, diffuse large B-cell lymphoma, adenoid cystic carcinoma of the salivary gland, Burkitt's lymphoma, multiple myeloma, pancreatic ductal adenocarcinoma, hairy cell leukemia, metastatic prostate cancer, melanoma, and colorectal cancer, and wherein, in the TYRO3 over-expressing cancer, TYRO3 is over-expressed by comparison to normal cells provided from the same tissue as the TYRO3 over-expressing cancer.

2. The method according to claim 1, wherein the inhibitor is selected from the group consisting of an antibody directed 10. The method according to claim 1, wherein said TYRO3 over-expressing cancer is bladder cancer.

11. The method according to claim 1, wherein said TYRO3 over-expressing cancer is diffuse large B-cell lymphoma.

12. The method according to claim 1, wherein said TYRO3 over-expressing cancer is adenoid cystic carcinoma of the salivary gland.

13. The method according to claim 1, wherein said TYRO3 over-expressing cancer is Burkitt's lymphoma.

14. The method according to claim 1, wherein said TYRO3 over-expressing cancer is multiple myeloma.

15. The method according to claim 1, wherein said TYRO3 over-expressing cancer is pancreatic ductal adenocarcinoma.

16. The method according to claim 1, wherein said TYRO3 over-expressing cancer is hairy cell leukemia.

17. The method according to claim 1, wherein said TYRO3 over-expressing cancer is metastatic prostate cancer.

18. The method according to claim 1, wherein said TYRO3 over-expressing cancer is melanoma.

19. The method according to claim 1, wherein said TYRO3 over-expressing cancer is colorectal cancer.

20. The method according to claim 2, wherein said antibody is an antibody designated as N-18 (Santa Cruz Biotechnology, Inc., Dallas, Tx).

21. The method according to claim 2, wherein said antibody is a humanized antibody.

22. The method according to claim 2, wherein said antibody is a chimeric antibody.

23. The method of claim 1, further comprising measuring the expression level of TYRO3 tyrosine kinase in a cancer sample from the subject, comparing the measured expression level of TYRO3 tyrosine kinase in said cancer sample to the expression level of TYRO3 tyrosine kinase in normal proliferative cell lines from the same tissue and administering a therapeutically effective amount of a composition comprising a TYRO3 inhibitor to a subject identified as having a TYRO3 tyrosine kinase over-expressing cancer.

\* \* \* \* \*

UNITED STATES PATENT AND TRADEMARK OFFICE
CERTIFICATE OF CORRECTION

| | | |
|---|---|---|
| PATENT NO. | : 9,233,144 B2 | Page 1 of 1 |
| APPLICATION NO. | : 13/062804 | |
| DATED | : January 12, 2016 | |
| INVENTOR(S) | : Isabelle Bernard-Pierrot et al. | |

It is certified that error appears in the above-identified patent and that said Letters Patent is hereby corrected as shown below:

Specification

Column 10,
Line 14, "21-23 by in length" should read --21-23 bp in length--.

Signed and Sealed this
Fifth Day of July, 2016

Michelle K. Lee
*Director of the United States Patent and Trademark Office*